US008980275B2

(12) United States Patent
Steadman et al.

(10) Patent No.: US 8,980,275 B2
(45) Date of Patent: Mar. 17, 2015

(54) TARGETED HETEROLOGOUS ANTIGEN PRESENTATION ON CALICIVIRUS VIRUS-LIKE PARTICLES

(75) Inventors: Bryan Steadman, Bozeman, MT (US); Ross Taylor, Bozeman, MT (US)

(73) Assignee: Takeda Vaccines, Inc., Bozeman, MT (US)

( * ) Notice: Subject to any disclaimer, the term of this patent is extended or adjusted under 35 U.S.C. 154(b) by 0 days.

(21) Appl. No.: 13/574,756

(22) PCT Filed: Jan. 21, 2011

(86) PCT No.: PCT/US2011/022094
§ 371 (c)(1),
(2), (4) Date: Nov. 7, 2012

(87) PCT Pub. No.: WO2011/091279
PCT Pub. Date: Jul. 28, 2011

(65) Prior Publication Data
US 2013/0052216 A1     Feb. 28, 2013

Related U.S. Application Data

(60) Provisional application No. 61/297,109, filed on Jan. 21, 2010.

(51) Int. Cl.
*A61K 39/12*     (2006.01)
*A61K 39/145*     (2006.01)
*A61K 39/155*     (2006.01)
*A61K 39/00*     (2006.01)

(52) U.S. Cl.
CPC .............. *A61K 39/145* (2013.01); *A61K 39/155* (2013.01); *A61K 2039/5256* (2013.01); *A61K 2039/5258* (2013.01); *A61K 2039/55505* (2013.01); *A61K 2039/55572* (2013.01); *C12N 2760/16134* (2013.01); *C12N 2770/16023* (2013.01); *C12N 2770/16034* (2013.01)
USPC ..................................... 424/192.1; 435/320.1

(58) Field of Classification Search
CPC ............ C12N 2770/16023; A61K 2039/5258; A61L 2300/258; A61L 27/54; A61L 31/16
See application file for complete search history.

(56) References Cited

U.S. PATENT DOCUMENTS

| 8,486,421 | B2 * | 7/2013 | Jiang et al. ................. 424/216.1 |
| 2003/0129588 | A1 | 7/2003 | Estes et al. |
| 2006/0177820 | A1 | 8/2006 | Takeda et al. |
| 2008/0299152 | A1 | 12/2008 | Richardson et al. |
| 2009/0280139 | A1 | 11/2009 | Jiang et al. |

FOREIGN PATENT DOCUMENTS

WO     WO9405700     *     3/1994     ............. C07K 15/00

OTHER PUBLICATIONS

Crisci et al. Chimeric calicivirus-like particles elicit protective antiviral cytotoxic responses without adjuvant. *Virology* May 10, 2009; vol. 387, No. 2, pp. 303-312.
Murata et al. Antigenic presentation of heterologous epitopes engineered into the outer surface-exposed helix 4 loop region of human papillomavirus L1 capsomeres. *Virology* Jun. 18, 2009, vol. 6, No. 81, pp. 1-10.
Allen et al. Characterisation of a GII-4 norovirus variant-specific surface-exposed site involved in antibody binding. *Virology* Sep. 25, 2009 vol. 6, No. 150, pp. 1-11.

* cited by examiner

*Primary Examiner* — Bao Li
(74) *Attorney, Agent, or Firm* — Cooley LLP

(57) ABSTRACT

The present invention provides particle-forming chimeric proteins comprising a Calicivirus capsid protein and one or more heterologous antigen sequences. In particular, the present invention discloses engineered Calicivirus capsid protein sequences containing heterologous epitopes fused at internal locations such that the modified capsid proteins retain the ability to form virus-like particles when expressed in host cells. Virus-like particles comprising the chimeric proteins and vaccine formulations are also described.

26 Claims, 18 Drawing Sheets

```
M M M A S K D A T S S V D G A S G A G Q L V P E V N A S D P L A M
D P V A G S S T A V A T A G Q V N P I D P W I I N N F V Q A P Q G
E F T I S P N N T P G D V L F D L S L G P H L N P F L L H L S Q M
Y N G W V G N M R V R I M L A G N A F T A G K I I V S C I P P G F
G S H N L T I A Q A T L F P H V I A D V R T L D P I E V P L E D V
R N V L F H N N D R N Q Q T M R L V C M L Y T P L R T G G G T G D
S F V V A G R V M T C P S P D F N F L F L V P P T V E Q K T R P F
T L P N L P L S S L S N S R A P L P I S S M G I S P D N V Q S V Q
F Q N G R C T L D G R L V G T T P V S L S H V A K I R G T S N G T
V I N L T E L D G T P F H P F E G P A P I G F P D L G G C D W H I
N M T Q F G H S S Q T Q Y D V D T T P D T F V P H L G S I Q A N G
I G S G N Y V G V L S W I S P P S H P S G S Q V D L W K I P N Y G
S S I T E A T H L A P S V Y P P G F G E V L V F F M S K M P G P G
A Y N L P C L L P Q E Y I S H L A S E Q A P T V G E A A L L H Y V
D P D T G R N L G E F K A Y P D G F L T C V P N G A S S G P Q Q L
P I N G V F V F V S W V S R F Y Q L K P V G T A S S A R G R L G L
R R (SEQ ID NO: 1)
```

B

```
M K M A S S D A N P S D G S T A N L V P E V N N E V M A L E P V V
G A A I A A P V A G Q Q N V I D P W I R N N F V Q A P G G E F T V
S P R N A P G E I L W S A P L G P D L N P Y L S H L A R M Y N G Y
A G G F E V Q V I L A G N A F T A G K I I F A A V P P N F P T E G
L S P S Q V T M F P H I I V D V R Q L E P V L I P L P D V R N N F
Y H Y N Q S N D P T I K L I A M L Y T P L R A N N A G D D V F T V
S C R V L T R P S P D F D F I F L V P P T V E S R T K P F T V P I
L T V E E M T N S R F P I P L E K L F T G P S G A F V V Q P Q N G
R C T T D G V L L G T T Q L S P V N I C T F R G D V T H I A G T Q
E Y T M N L A S Q N W N N Y D P T E E I P A P L G T P D F V G K I
Q G V L T Q T T R G D G S T R G H K A T V S T G S V H F T P K L G
S V Q F S T D T S N D F E T G Q N T K F T P V G V V Q D G S T T H
Q N E P Q Q W V L P D Y S G R D S H N V H L A P A V A P T F P G E
Q L L F F R S T M P G C S G Y P N M N L D C L L P Q E W V Q H F Y
Q E A A P A Q S D V A L L R F V N P D T G R V L F E C K L H K S G
Y V T V A H T G Q H D L V I P P N G Y F R F D S W V N Q F Y T L A
P M G N G T G R R R A L (SEQ ID NO: 2)
```

FIGURE 3
A
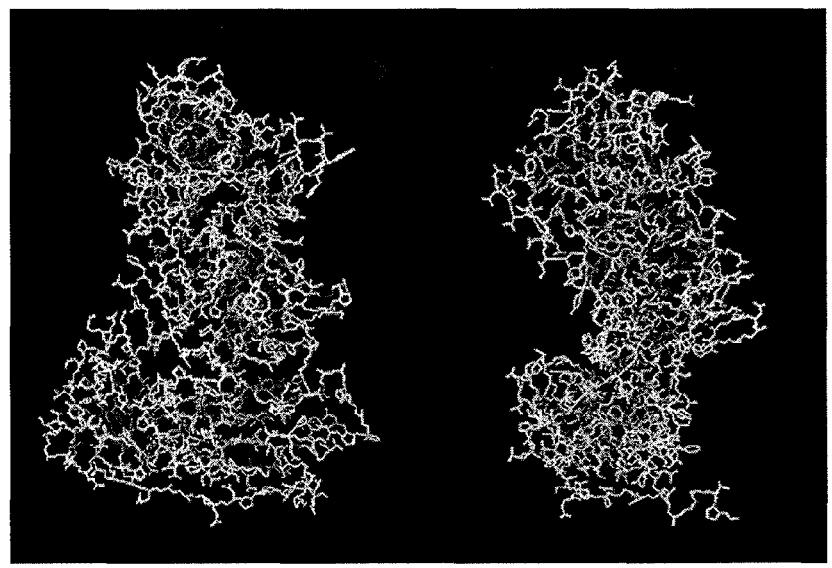
B
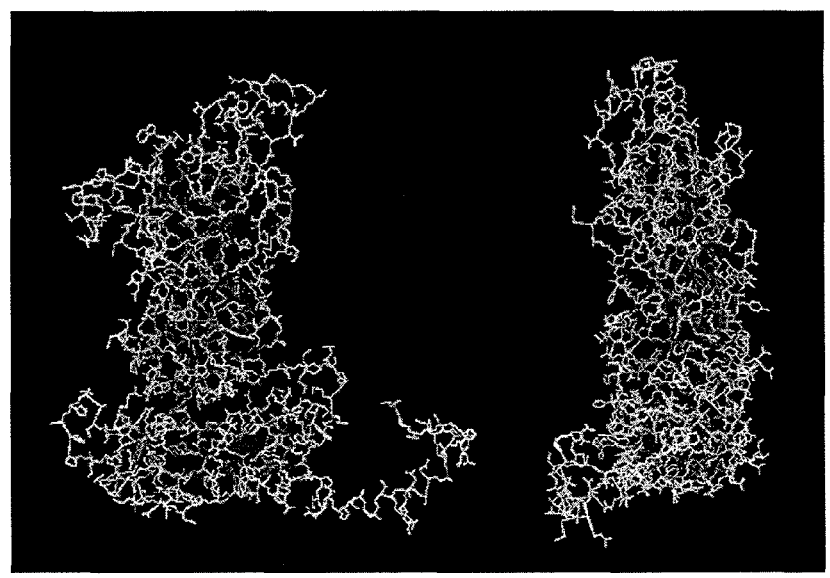

```
M E G N G L P Q A G Q Q Q A L D V P G T T G P T S S A V V V A N P
D Q P S A Q A Q R M E L A V A T G A V S S N V P D A V R Q C F A L
L R T F P W N T R Q A T G T Y L G S A A L S P A L N P Y T A H L S
A M W A G W G G S M E A R V T I S G S G T F A G K I I V A L L P P
G L D P T R V R D P G V L P H A Q V D A R A V D P I T F N I N D V
R A V D Y H R T D G Q E A T S T L G F W V L Q P L I N P F S H D A
L S T A W V S V E T R P G P D F D F C L L K P P Q M E M E N G L S
P S T L L P R H L G R S R G N R C G G F I V G M A V V A M A H Q V
N H H F S T A A T T Y G W S T L P L G P C A A K I T S S L P G E I
N N Y T G F A D V D G A G E G P I M P N I P N H W P D S C A S S V
I A T W D S S L H R P N L G I S G S I M T F D N H G D A D E A Q I
T G A M A A T V D P S P S R R T Q L Q G S F T A N T M R I M R T S
G L D K I G E V N K N V Y F I P I L L D G A T G Y I N E K V T N L
A D I N I S Y G P V G S N N V I L W R E R V F S S H P R P G I L Y
S S Q L E S T A S I F Q D G P V N I P N N Y M A V F N V S D T G A
D F Q I G I C P D G Y M R T G S P V G T V V D L T P E C T F T F V
G L F P F T S P L N G P H G T G R G R S V Y Q  (SEQ ID NO: 3)
```

B

```
M E G N G L P Q A G Q Q Q A L D V P G T T G P T S S A V V V A N P
D Q P S A Q A Q R M E L A V A T G A V S S N V P D A V R Q C F A L
L R T F P W N T R Q A T G T Y L G S A A L S P A L N P Y T A H L S
A M W A G W G G S M E A R V T I S G S G T F A G K I I V A L L P P
G L D P T R V R D P G V L P H A Q V D A R A V D P I T F N I N D V
R A V D Y H R T D G Q E A T S T L G F W V L Q P L I N P F S H D A
L S T A W V S V E T R P G P D F D F C L L K P P Q M E M E N G L S
P S T L L P R H L G R S R G N R C G G F I V G M A V V A M A H Q V
N H H F S T A A T T Y G W S T L P L G P C A A K I T S S L P G E I
N N Y T G F A D V D G A G E G P I M P N I P N H W P D S C A S S V
I A T W D S S L H R P N L G I S G S I M T F D N H G D A D E A Q I
T G A M A A T V D P S P S R R T Q L Q G S F T A N T M R I M R T S
G L D K I G E V N K N V Y F I P I L L D G A T G Y I N E K V T N L
A D I N I S Y G P V G S N N V I L W R E R V F S S H P R P G I L Y
S S Q L E S T A S I F Q D G P V N I P N N Y M A V F N V S D T G A
D F Q I G I C P D G Y M R T G S P V G T V V D L T P E C T F T F V
G L F P F T S P L N G P H G T G R G R S V Y Q  (SEQ ID NO: 3)
```

FIGURE 5

```
Norwalk   MMMASKDATSSVDGASGAGQLVPEVNASDPLAMDPVAGSSTAVATAGQVNPIDPWIINNF
SMSV      -----------SDGPGSAEIVTEEQGTVVQQQPAPAPTALATLATASTGKSVEQEWMTFF
                     **...*   :.  *  .:           *.. :  :::***.  :.::      :.  *

Norwalk   VQAPQGEFTISPNNTPGDVLFDLSLGPHLNPFLLHLSQMYNGWVGNMRVRIMLAGNAFTA
SMSV      SYHTSINWSTVE--SQGKILYSQALNPSINPYLDHIAKLYSTWSGGIDVRFTVSGSGVFG
                     .. :::        : *.:*:. :*.* :**:* *::::*. * *.: **: ::*... .

Norwalk   GKIIVSCIPPGFGSHNLTIAQATLFPHVIADVRTLDPIEVPLEDVRNVLFHNNDRNQQTM
SMSV      GKLAALLVPP--GVEPIESVSMLQYPHVLFDARQTEPVIFTIPDIRKTLFHSMDET-DTT
          **:  .  :**  *  .  :  ..    :***: *.*  :*: ..: *:*:.***. *.. :*

Norwalk   RLVCMLYTPLR--TGGGTGDSFVVAGRVMTCPSPDFNFLFLVPP--TVEQKTRPFTLPNL
SMSV      KLVIMVYNELINPYENGVENKTTCSITVETRPSADFTFALLKPPGSLIKHGSIPSDLIPR
          :** *:*. *       .*. :..  :  * * **.**.* :* **   ::: : * *

Norwalk   PLSSLSNSRAPLPISSMGISPDNVQS-VQFQNGRCTLDGRLVGTTPVSLSHVAKIRGTSN
SMSV      NSAHWMGNRWWSTISGFSVQPRVFQSNRHFDFDSTTTGWSTPYYVPIEIKIQGKVGSNNK
             :    ..*    .**.::..*   .** :*: .  *   ..    .*::.  .*:   ...:

Norwalk   GTVINLTELDGTPFHPFEGPAPIGFPDLGGCDWHINMTQFGHSSQTQYDVDTTPDTFVPH
SMSV      WFHVIDTDKALVPGIPDGWPDTTIPDETKATNGNESYGESYRAGSTTIKPNENSTHFKGT
             :  *:    .*    *     *.      :       . .:::.      :   ::..*   . :  ..    *

Norwalk   LGSIQANGIGSGN-------------------YVGVLSWISPPSHPSGSQVDLWKIPNY
SMSV      YICGTLSTVEIPENDEQQIKTEAEKKSQTMYVVTADFKDTIVKPQHKISPQKLVVYFDGP
                .    . :   :                  ... *  *.*  ..*   :  :  .

Norwalk   GSSITEATHLAPS----VYPPGFGEVLVFFMSKMPGPGAYNLPCLLPQEYISHLASEQAP
SMSV      EKDLTMSATLSPLGYTLVDEQPVGSVSSRVVRIATLPEAFTQGGNYPIFYVNKIKVGYFD
          ..:*  :: *:*     *   .*.*  .:    . * *:.      *  *:..::

Norwalk   TVGEAALLHYVDPDTGRNLG-EFKAYPDGFLTCVPNGASSGPQQLPINGVFVFVSWVSRF
SMSV      RATTNCYNSQILMTSQRLAEGNYNLPPDSLAVYRITDSSSQWFDIGINHDGFSYVGLSDL
            .     .   :   : *       :::   **.: .    ..:**    :: **    .    :* :

Norwalk   YQLKPVGTASSARGRLGLRR--------------- (SEQ ID NO: 1)
SMSV      PNDLSFPLTSTFMGVQLARVKLASKVKAHTITAK  (SEQ ID NO: 4)
```

FIGURE 14

NW-RSV 29mer chimera: 308-309 insertion

Norwalk VLP

SEQUENCE LISTING

<160> NUMBER OF SEQ ID NOS: 7

<210> SEQ ID NO 1
<211> LENGTH: 530
<212> TYPE: PRT
<213> ORGANISM: Norovirus Norwalk virus sp.

<400> SEQUENCE: 1

```
Met Met Met Ala Ser Lys Asp Ala Thr Ser Ser Val Asp Gly Ala Ser
1               5                   10                  15

Gly Ala Gly Gln Leu Val Pro Glu Val Asn Ala Ser Asp Pro Leu Ala
            20                  25                  30

Met Asp Pro Val Ala Gly Ser Ser Thr Ala Val Ala Thr Ala Gly Gln
        35                  40                  45

Val Asn Pro Ile Asp Pro Trp Ile Ile Asn Asn Phe Val Gln Ala Pro
    50                  55                  60

Gln Gly Glu Phe Thr Ile Ser Pro Asn Asn Thr Pro Gly Asp Val Leu
65                  70                  75                  80

Phe Asp Leu Ser Leu Gly Pro His Leu Asn Pro Phe Leu Leu His Leu
                85                  90                  95

Ser Gln Met Tyr Asn Gly Trp Val Gly Asn Met Arg Val Arg Ile Met
            100                 105                 110

Leu Ala Gly Asn Ala Phe Thr Ala Gly Lys Ile Ile Val Ser Cys Ile
        115                 120                 125

Pro Pro Gly Phe Gly Ser His Asn Leu Thr Ile Ala Gln Ala Thr Leu
    130                 135                 140

Phe Pro His Val Ile Ala Asp Val Arg Thr Leu Asp Pro Ile Glu Val
145                 150                 155                 160

Pro Leu Glu Asp Val Arg Asn Val Leu Phe His Asn Asn Asp Arg Asn
                165                 170                 175

Gln Gln Thr Met Arg Leu Val Cys Met Leu Tyr Thr Pro Leu Arg Thr
            180                 185                 190

Gly Gly Gly Thr Gly Asp Ser Phe Val Val Ala Gly Arg Val Met Thr
        195                 200                 205

Cys Pro Ser Pro Asp Phe Asn Phe Leu Phe Leu Val Pro Pro Thr Val
    210                 215                 220
```

-continued

```
Glu Gln Lys Thr Arg Pro Phe Thr Leu Pro Asn Leu Pro Leu Ser Ser
225                 230                 235                 240

Leu Ser Asn Ser Arg Ala Pro Leu Pro Ile Ser Ser Met Gly Ile Ser
                245                 250                 255

Pro Asp Asn Val Gln Ser Val Gln Phe Gln Asn Gly Arg Cys Thr Leu
            260                 265                 270

Asp Gly Arg Leu Val Gly Thr Thr Pro Val Ser Leu Ser His Val Ala
        275                 280                 285

Lys Ile Arg Gly Thr Ser Asn Gly Thr Val Ile Asn Leu Thr Glu Leu
    290                 295                 300

Asp Gly Thr Pro Phe His Pro Phe Glu Gly Pro Ala Pro Ile Gly Phe
305                 310                 315                 320

Pro Asp Leu Gly Gly Cys Asp Trp His Ile Asn Met Thr Gln Phe Gly
                325                 330                 335

His Ser Ser Gln Thr Gln Tyr Asp Val Asp Thr Thr Pro Asp Thr Phe
            340                 345                 350

Val Pro His Leu Gly Ser Ile Gln Ala Asn Gly Ile Gly Ser Gly Asn
        355                 360                 365

Tyr Val Gly Val Leu Ser Trp Ile Ser Pro Pro Ser His Pro Ser Gly
    370                 375                 380

Ser Gln Val Asp Leu Trp Lys Ile Pro Asn Tyr Gly Ser Ser Ile Thr
385                 390                 395                 400

Glu Ala Thr His Leu Ala Pro Ser Val Tyr Pro Pro Gly Phe Gly Glu
                405                 410                 415

Val Leu Val Phe Phe Met Ser Lys Met Pro Gly Pro Gly Ala Tyr Asn
            420                 425                 430

Leu Pro Cys Leu Leu Pro Gln Glu Tyr Ile Ser His Leu Ala Ser Glu
        435                 440                 445

Gln Ala Pro Thr Val Gly Glu Ala Ala Leu Leu His Tyr Val Asp Pro
    450                 455                 460

Asp Thr Gly Arg Asn Leu Gly Glu Phe Lys Ala Tyr Pro Asp Gly Phe
465                 470                 475                 480

Leu Thr Cys Val Pro Asn Gly Ala Ser Ser Gly Pro Gln Gln Leu Pro
                485                 490                 495

Ile Asn Gly Val Phe Val Phe Val Ser Trp Val Ser Arg Phe Tyr Gln
            500                 505                 510

Leu Lys Pro Val Gly Thr Ala Ser Ser Ala Arg Gly Arg Leu Gly Leu
        515                 520                 525

Arg Arg
    530

<210> SEQ ID NO 2
<211> LENGTH: 540
<212> TYPE: PRT
<213> ORGANISM: Artificial Sequence
<220> FEATURE:
<223> OTHER INFORMATION: Composite GII.4 Norovirus VP1 amino acid
      sequence

<400> SEQUENCE: 2

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45
```

```
Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
                100                 105                 110

Ala Phe Thr Ala Gly Lys Ile Ile Phe Ala Ala Val Pro Pro Asn Phe
                115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp
145                 150                 155                 160

Val Arg Asn Asn Phe Tyr His Tyr Asn Gln Ser Asn Asp Pro Thr Ile
                165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
                195                 200                 205

Asp Phe Asp Phe Ile Phe Leu Val Pro Pro Thr Val Glu Ser Arg Thr
    210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
                275                 280                 285

Asp Val Thr His Ile Ala Gly Thr Gln Glu Tyr Thr Met Asn Leu Ala
    290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
                340                 345                 350

Thr Gly Ser Val His Phe Thr Pro Lys Leu Gly Ser Val Gln Phe Ser
                355                 360                 365

Thr Asp Thr Ser Asn Asp Phe Glu Thr Gly Gln Asn Thr Lys Phe Thr
    370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asn
                435                 440                 445

Leu Asp Cys Leu Leu Pro Gln Glu Trp Val Gln His Phe Tyr Gln Glu
    450                 455                 460
```

```
Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
            500                 505                 510

Gly Tyr Phe Arg Phe Asp Ser Trp Val Asn Gln Phe Tyr Thr Leu Ala
        515                 520                 525

Pro Met Gly Asn Gly Thr Gly Arg Arg Arg Ala Leu
530                 535                 540

<210> SEQ ID NO 3
<211> LENGTH: 551
<212> TYPE: PRT
<213> ORGANISM: Sapovirus sp.

<400> SEQUENCE: 3

Met Glu Gly Asn Gly Leu Pro Gln Ala Gly Gln Gln Gln Ala Leu Asp
1               5                   10                  15

Val Pro Gly Thr Thr Gly Pro Thr Ser Ser Ala Val Val Val Ala Asn
            20                  25                  30

Pro Asp Gln Pro Ser Ala Gln Ala Gln Arg Met Glu Leu Ala Val Ala
        35                  40                  45

Thr Gly Ala Val Ser Ser Asn Val Pro Asp Ala Val Arg Gln Cys Phe
50                  55                  60

Ala Leu Leu Arg Thr Phe Pro Trp Asn Thr Arg Gln Ala Thr Gly Thr
65                  70                  75                  80

Tyr Leu Gly Ser Ala Ala Leu Ser Pro Ala Leu Asn Pro Tyr Thr Ala
                85                  90                  95

His Leu Ser Ala Met Trp Ala Gly Trp Gly Ser Met Glu Ala Arg
            100                 105                 110

Val Thr Ile Ser Gly Ser Gly Thr Phe Ala Gly Lys Ile Ile Val Ala
        115                 120                 125

Leu Leu Pro Pro Gly Leu Asp Pro Thr Arg Val Arg Asp Pro Gly Val
130                 135                 140

Leu Pro His Ala Gln Val Asp Ala Arg Ala Val Asp Pro Ile Thr Phe
145                 150                 155                 160

Asn Ile Asn Asp Val Arg Ala Val Asp Tyr His Arg Thr Asp Gly Gln
                165                 170                 175

Glu Ala Thr Ser Thr Leu Gly Phe Trp Val Leu Gln Pro Leu Ile Asn
            180                 185                 190

Pro Phe Ser His Asp Ala Leu Ser Thr Ala Trp Val Ser Val Glu Thr
        195                 200                 205

Arg Pro Gly Pro Asp Phe Asp Phe Cys Leu Leu Lys Pro Pro Gln Met
210                 215                 220

Glu Met Glu Asn Gly Leu Ser Pro Ser Thr Leu Leu Pro Arg His Leu
225                 230                 235                 240

Gly Arg Ser Arg Gly Asn Arg Cys Gly Gly Phe Ile Val Gly Met Ala
                245                 250                 255

Val Val Ala Met Ala His Gln Val Asn His His Phe Ser Thr Ala Ala
            260                 265                 270

Thr Thr Tyr Gly Trp Ser Thr Leu Pro Leu Gly Pro Cys Ala Ala Lys
        275                 280                 285

Ile Thr Ser Ser Leu Pro Gly Glu Ile Asn Asn Tyr Thr Gly Phe Ala
290                 295                 300
```

-continued

```
Asp Val Asp Gly Ala Gly Glu Gly Pro Ile Met Pro Asn Ile Pro Asn
305                 310                 315                 320

His Trp Pro Asp Ser Cys Ala Ser Ser Val Ile Ala Thr Trp Asp Ser
            325                 330                 335

Ser Leu His Arg Pro Asn Leu Gly Ile Ser Gly Ser Ile Met Thr Phe
        340                 345                 350

Asp Asn His Gly Asp Ala Asp Glu Ala Gln Ile Thr Gly Ala Met Ala
    355                 360                 365

Ala Thr Val Asp Pro Ser Pro Ser Arg Arg Thr Gln Leu Gln Gly Ser
370                 375                 380

Phe Thr Ala Asn Thr Met Arg Ile Met Arg Thr Ser Gly Leu Asp Lys
385                 390                 395                 400

Ile Gly Glu Val Asn Lys Asn Val Tyr Phe Ile Pro Ile Leu Leu Asp
                405                 410                 415

Gly Ala Thr Gly Tyr Ile Asn Glu Lys Val Thr Asn Leu Ala Asp Ile
            420                 425                 430

Asn Ile Ser Tyr Gly Pro Val Gly Ser Asn Val Ile Leu Trp Arg
        435                 440                 445

Glu Arg Val Phe Ser Ser His Pro Arg Pro Gly Ile Leu Tyr Ser Ser
    450                 455                 460

Gln Leu Glu Ser Thr Ala Ser Ile Phe Gln Asp Gly Pro Val Asn Ile
465                 470                 475                 480

Pro Asn Asn Tyr Met Ala Val Phe Asn Val Ser Asp Thr Gly Ala Asp
                485                 490                 495

Phe Gln Ile Gly Ile Cys Pro Asp Gly Tyr Met Arg Thr Gly Ser Pro
            500                 505                 510

Val Gly Thr Val Val Asp Leu Thr Pro Glu Cys Thr Phe Thr Phe Val
        515                 520                 525

Gly Leu Phe Pro Phe Thr Ser Pro Leu Asn Gly Pro His Gly Thr Gly
    530                 535                 540

Arg Gly Arg Ser Val Tyr Gln
545                 550
```

<210> SEQ ID NO 4
<211> LENGTH: 558
<212> TYPE: PRT
<213> ORGANISM: Vesivirus San Miguel sea lion sp.

<400> SEQUENCE: 4

```
Ser Asp Gly Pro Gly Ser Ala Glu Ile Val Thr Glu Glu Gln Gly Thr
1               5                   10                  15

Val Val Gln Gln Gln Pro Ala Pro Ala Pro Thr Ala Leu Ala Thr Leu
                20                  25                  30

Ala Thr Ala Ser Thr Gly Lys Ser Val Glu Gln Glu Trp Met Thr Phe
            35                  40                  45

Phe Ser Tyr His Thr Ser Ile Asn Trp Ser Thr Val Glu Ser Gln Gly
        50                  55                  60

Lys Ile Leu Tyr Ser Gln Ala Leu Asn Pro Ser Ile Asn Pro Tyr Leu
65                  70                  75                  80

Asp His Ile Ala Lys Leu Tyr Ser Thr Trp Ser Gly Gly Ile Asp Val
                85                  90                  95

Arg Phe Thr Val Ser Gly Ser Gly Val Phe Gly Gly Lys Leu Ala Ala
            100                 105                 110

Leu Leu Val Pro Pro Gly Val Glu Pro Ile Glu Ser Val Ser Met Leu
        115                 120                 125
```

```
Gln Tyr Pro His Val Leu Phe Asp Ala Arg Gln Thr Glu Pro Val Ile
            130                 135                 140

Phe Thr Ile Pro Asp Ile Arg Lys Thr Leu Phe His Ser Met Asp Glu
145                 150                 155                 160

Thr Asp Thr Thr Lys Leu Val Ile Met Val Tyr Asn Glu Leu Ile Asn
                165                 170                 175

Pro Tyr Glu Asn Gly Val Glu Asn Lys Thr Thr Cys Ser Ile Thr Val
            180                 185                 190

Glu Thr Arg Pro Ser Ala Asp Phe Thr Phe Ala Leu Leu Lys Pro Pro
            195                 200                 205

Gly Ser Leu Ile Lys His Gly Ser Ile Pro Ser Asp Leu Ile Pro Arg
210                 215                 220

Asn Ser Ala His Trp Met Gly Asn Arg Trp Ser Thr Ile Ser Gly
225                 230                 235                 240

Phe Ser Val Gln Pro Arg Val Phe Gln Ser Asn Arg His Phe Asp Phe
                245                 250                 255

Asp Ser Thr Thr Thr Gly Trp Ser Thr Pro Tyr Tyr Val Pro Ile Glu
            260                 265                 270

Ile Lys Ile Gln Gly Lys Val Gly Ser Asn Asn Lys Trp Phe His Val
            275                 280                 285

Ile Asp Thr Asp Lys Ala Leu Val Pro Gly Ile Pro Asp Gly Trp Pro
290                 295                 300

Asp Thr Thr Ile Pro Asp Glu Thr Lys Ala Thr Asn Gly Asn Phe Ser
305                 310                 315                 320

Tyr Gly Glu Ser Tyr Arg Ala Gly Ser Thr Thr Ile Lys Pro Asn Glu
                325                 330                 335

Asn Ser Thr His Phe Lys Gly Thr Tyr Ile Cys Gly Thr Leu Ser Thr
            340                 345                 350

Val Glu Ile Pro Glu Asn Asp Glu Gln Gln Ile Lys Thr Glu Ala Glu
            355                 360                 365

Lys Lys Ser Gln Thr Met Tyr Val Val Thr Ala Asp Phe Lys Asp Thr
370                 375                 380

Ile Val Lys Pro Gln His Lys Ile Ser Pro Gln Lys Leu Val Val Tyr
385                 390                 395                 400

Phe Asp Gly Pro Glu Lys Asp Leu Thr Met Ser Ala Thr Leu Ser Pro
                405                 410                 415

Leu Gly Tyr Thr Leu Val Asp Glu Gln Pro Val Gly Ser Val Ser Ser
            420                 425                 430

Arg Val Val Arg Ile Ala Thr Leu Pro Glu Ala Phe Thr Gln Gly Gly
            435                 440                 445

Asn Tyr Pro Ile Phe Tyr Val Asn Lys Ile Lys Val Gly Tyr Phe Asp
450                 455                 460

Arg Ala Thr Thr Asn Cys Tyr Asn Ser Gln Ile Leu Met Thr Ser Gln
465                 470                 475                 480

Arg Leu Ala Glu Gly Asn Tyr Asn Leu Pro Asp Ser Leu Ala Val
                485                 490                 495

Tyr Arg Ile Thr Asp Ser Ser Ser Gln Trp Phe Asp Ile Gly Ile Asn
            500                 505                 510

His Asp Gly Phe Ser Tyr Val Gly Leu Ser Asp Leu Pro Asn Asp Leu
            515                 520                 525
```

```
Ser Phe Pro Leu Thr Ser Thr Phe Met Gly Val Gln Leu Ala Arg Val
        530                 535                 540

Lys Leu Ala Ser Lys Val Lys Ala His Thr Ile Thr Ala Lys
545                 550                 555

<210> SEQ ID NO 5
<211> LENGTH: 9
<212> TYPE: PRT
<213> ORGANISM: Artificial Sequence
<220> FEATURE:
<223> OTHER INFORMATION: influenza hemagglutinin antigen epitope

<400> SEQUENCE: 5

Tyr Pro Tyr Asp Val Pro Asp Tyr Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Respiratory syncytial virus F protein antigenic
      epitope

<400> SEQUENCE: 6

Leu Ile Asn Asp Met Pro Ile Thr Asn
1               5

<210> SEQ ID NO 7
<211> LENGTH: 29
<212> TYPE: PRT
<213> ORGANISM: Artificial Sequence
<220> FEATURE:
<223> OTHER INFORMATION: Respiratory syncytial virus F protein antigenic
      epitope

<400> SEQUENCE: 7

Tyr Met Leu Thr Asn Ser Glu Leu Leu Ser Leu Ile Asn Asp Met Pro
1               5                   10                  15

Ile Thr Asn Asp Gln Lys Lys Leu Met Ser Asn Asn Val
            20                  25
```

TARGETED HETEROLOGOUS ANTIGEN PRESENTATION ON CALICIVIRUS VIRUS-LIKE PARTICLES

CROSS REFERENCE TO RELATED APPLICATIONS

This application is a national stage application of International Application No. PCT/US2011/022094, filed Jan. 21, 2011, which claims die benefit of U.S. Provisional Application No. 61/297,109, filed Jan. 21, 2010, each of which is herein incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LIGO_023_01US_SeqList_ST25.txt, date recorded: Jul. 23, 2012, file size 20 kilobytes).

FIELD OF THE INVENTION

The present invention relates to the fields of virology, molecular biology and vaccine development. In particular, the present invention relates to Calicivirus capsid proteins that can be modified to insert heterologous antigen epitopes into the protein sequence such that the heterologous antigen epitopes can be displayed on the surface of virus-like particles generated from the modified capsid proteins. Such modified capsid proteins and virus-like particles are useful in vaccine formulations.

BACKGROUND OF THE INVENTION

Many current vaccines employ attenuated microorganisms to induce protective immune responses against pathogens. Although these types of vaccines typically produce strong immune responses, there is a potential risk of infection due to the possibility of a reversion back to a virulent microoraganism, and therefore these vaccines may be contraindicated in some patient populations. Other vaccines that utilize recombinant antigens avoid the risk of infection, but generally produce weaker immune responses than live attenuated vaccines. Such weak immune responses with recombinant antigens are thought to be due to ineffective presentation of the antigens to the immune system. Thus, vaccine platforms that are better able to mimic the presentation of antigens to the immune system as occurs during natural infection are needed.

In recent years, virus-like particles (VLPs) or pseudovirions have been used to present antigens to induce an effective immune response. VLPs and pseudovirions structurally resemble naturally-occurring, infectious particles, but do not contain the necessary viral genetic information for replication. Immune responses to antigens presented on VLPs or pseudovirions are typically much greater than responses to soluble antigens. Although VLPs appear to be a useful platform for effectively presenting antigens to the immune system, efficient production of VLPs have proven difficult to achieve for some viruses. Furthermore, manipulation of viral capsid protein sequences and incorporation of foreign antigenic proteins or fragments into the viral particles often eliminates or reduces the efficient generation of intact VLPs.

Thus, there is a continuing need in the art to develop viable, safe vaccine platforms that effectively present antigens to the immune system without the associated risks of live attenuated vaccines. Furthermore, vaccine platforms in which any antigen of interest or multiple antigens from different pathogenic organisms can easily be incorporated are desirable.

SUMMARY OF THE INVENTION

The present invention is based, in part, on the discovery that heterologous antigenic epitopes can be inserted into the capsid protein of Calicivirus such that the capsid protein retains the ability to form VLPs. Accordingly, the present invention provides a chimeric protein comprising a Calicivirus capsid protein and at least one heterologous antigen or fragment thereof, wherein the chimeric protein is capable of forming VLPs when expressed in a host cell.

In one embodiment, at least one heterologous antigen or fragment thereof is inserted into a P2 domain of the Calicivirus capsid protein. In another embodiment, at least one heterologous antigen or fragment thereof is inserted into one or more solvent-exposed loops of the P2 domain of the Calicivirus capsid protein. The Calicivirus can be, for example, a Norovirus, a Sapovirus, a Lagovirus, or a Vesivirus.

The heterologous antigen or fragment thereof can be inserted directly into the amino acid sequence of a Calicivirus capsid sequence without deleting any amino acids from the capsid sequence. Alternatively, the heterologous antigen or fragment replaces one or more residues of the Calicivirus capsid protein. The heterologous antigen can be derived from various pathogens, such as viruses, bacteria, and eukaryotic pathogens. In some embodiments, the heterologous antigen can be derived from tumor-associated antigens or allergens. The heterologous antigen may be a T-cell or B-cell stimulating epitope.

The present invention also includes virus-like particles comprising chimeric capsid proteins of the invention as well as isolated nucleic acids and vectors encoding the novel chimeric capsid proteins. In some embodiments, the chimeric capsid protein comprises a capsid protein derived from Norovirus and at least one heterologous antigen or fragment thereof. The Norovirus may be, for example, a Genogroup I or Genogroup II Norovirus.

The present invention provides a vaccine formulation comprising virus-like particles containing the chimeric proteins of the invention. In some embodiments, the vaccine formulation further comprises an adjuvant. The vaccine formulation may be a liquid formulation or a dry powder formulation. Methods of inducing an immune response to a foreign agent by administering vaccine formulations as described herein are also encompassed by the present invention.

The present invention also includes a method of making a chimeric virus-like particle. In one embodiment, the method comprises expressing a chimeric protein as described herein in a host cell, and growing the host cell in conditions in which virus-like particles are formed. In some embodiments, the host cell is an insect cell.

BRIEF DESCRIPTION OF THE FIGURES

FIG. 1. A. Solvent-accessible P2 domain loops in the GI.1 Norovirus Norwalk VP1 subunit. Amino acid sequence of GI.1 Norwalk VP1 capsid protein (SEQ ID NO: 1). P2 domain residues are shaded in grey, while solvent-accessible loop residues within this domain are underlined and bolded. B. Solvent-accessible P2 domain loop in the Norovirus GII.4 consensus VP1 subunit. Amino acid sequence of a GII.4 consensus VP1 capsid protein (SEQ ID NO: 2). P2 domain residues are shaded in grey, while solvent-accessible loop residues within this domain are underlined and bolded.

FIG. 3. A. Structure model of the Sapovirus Hu/Yokohama16-4/2007/JP VP1 subunit using the Norwalk VP1 atomic structure as a template. B. Structure model of the Sapovirus Hu/Yokohama16-4/2007/JP VP1 subunit using the SMSV VP1 atomic structure as a template.

FIG. 4. A. Solvent-accessible P2 domain loops in the Sapovirus Hu/Yokohama16-4/2007/JP VP1 subunit using the Norwalk VP1 atomic structure as a template. Amino acid sequence of Sapovirus Hu/Yokohama16-4/2007/JP VP1 capsid protein (SEQ ID NO: 3). Based on the Norwalk VP1 template, P2 domain residues are shaded in grey, while solvent-accessible loop residues within this domain are underlined and bolded. B. Solvent-accessible P2 domain loops in the Sapovirus Hu/Yokohama16-4/2007/JP VP1 subunit using the SMSV VP1 atomic structure as a template. Amino acid sequence of Sapovirus Hu/Yokohama16-4/2007/JP VP1 capsid protein (SEQ ID NO: 3). Based on the SMSV VP1 template, P2 domain residues are shaded in grey, while solvent-accessible loop residues within this domain are underlined and bolded.

FIG. 5. Amino acid sequence alignment between Norovirus Norwalk (SEQ ID NO: 1) and Vesivirus San Miguel sea lion (SMSV; SEQ ID NO: 4) VP1 capsid proteins. Asterisks denote identical residues; colons denote conservative substitutions; periods denote semi-conservative substitutions; and blank spaces denote non-conservative substitutions.

FIG. 14. Analysis of chimeric Norovirus VLPs (containing a 29 residue RSV-F protein epitope) by electron microscopy.

DETAILED DESCRIPTION OF THE INVENTION

Figure 2:
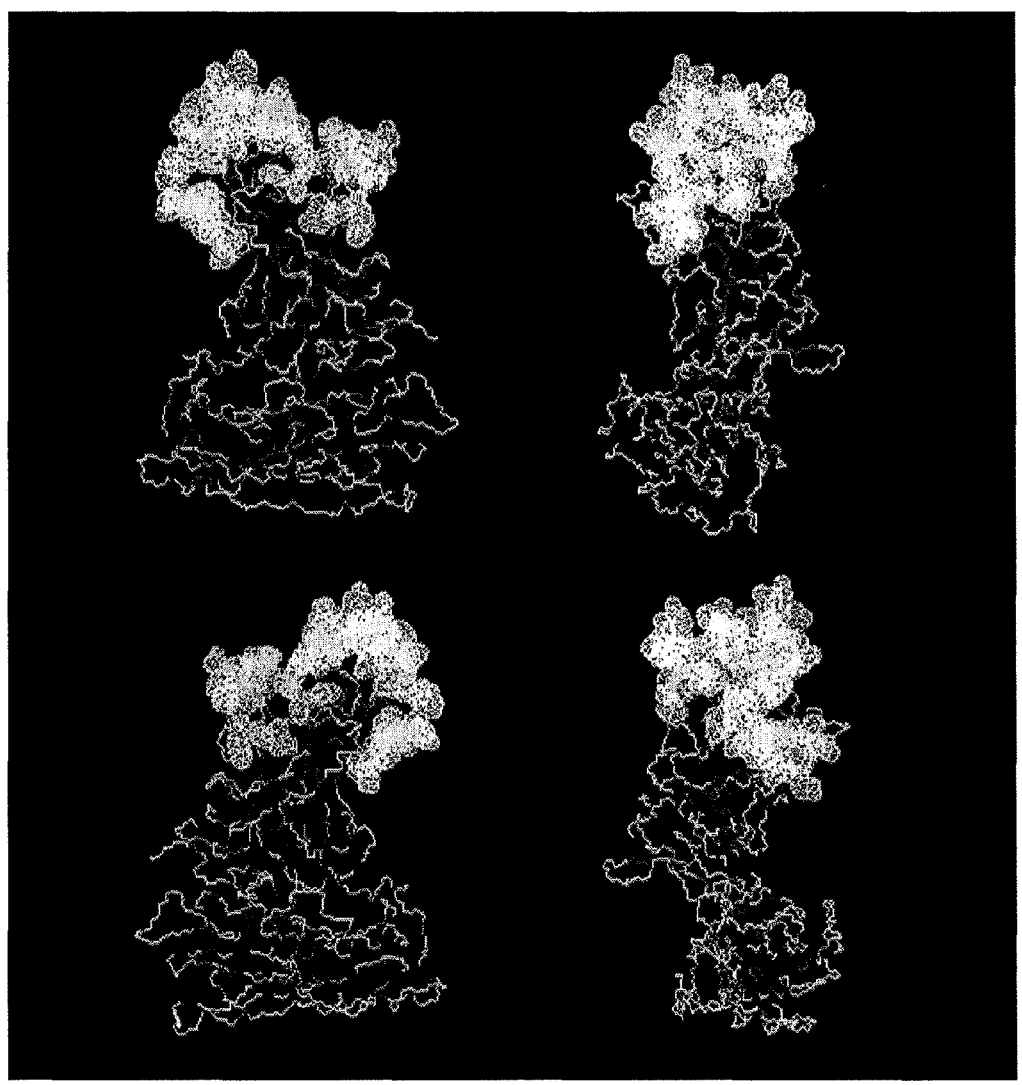
FIG. 2. Structure model of the Norovirus GII.4 consensus VP1 subunit with identified solvent-accessible P2 domain loops highlighted.

The present invention is based on the discovery that heterologous peptides can be inserted into particular, solvent-exposed regions of Calicivirus capsid proteins such that the capsid proteins retain the ability to form VLPs. The present inventors have developed effective strategies to engineer Calicivirus capsid proteins such that one or more heterologous antigens are effectively displayed on the surface of VLPs formed from modified capsid proteins. Thus, the present invention provides novel chimeric proteins comprising a capsid protein derived from a Calicivirus and at least one heterologous antigen or fragment thereof, wherein the chimeric proteins are capable of forming VLPs when expressed in a host cell.

As used herein, a "chimeric protein" refers to a fusion protein comprising peptides from two or more organisms. The two or more peptides can be fused at their amino or carboxy termini. Alternatively, one or more of the peptides may be fused at an internal location within another peptide. Preferably, the chimeric proteins of the invention comprise a capsid protein or portion thereof derived from a Calicivirus. The Calicivirus or Caliciviridae family includes Vesivirus, Norovirus, Lagovirus, and Sapovirus genera. The capsid protein of the chimeric proteins of the invention may be derived from a capsid protein from any of these four genera. For instance, in some embodiments, the capsid protein is derived from San Miguel sea lion virus, a Vesivirus. In one embodiment, the capsid protein has a sequence of SEQ ID NO: 4.

In certain embodiments, the capsid protein is derived from a Norovirus. The Norovirus genus is divided into five genogroups (GI, GII, GIII, GIV, and GV). GI, GII, and GIV Noroviruses are infectious in humans, while GIII Noroviruses primarily infect bovine species. GV has recently been isolated from mice (Zheng et al. (2006) Virology, Vol 346: 312-323). Representative of GIII are the Jena and Newbury strains, while the Alphatron, Fort Lauderdale, and Saint Cloud strains are representative of GIV. The GI and GII groups may be further segregated into genetic clusters or genotypes based on genetic classification (Ando et al. (2000) J. Infectious Diseases, Vol. 181(Supp2):S336-5348; Lindell et al. (2005) J. Clin. Microbiol., Vol. 43(3): 1086-1092). As used herein, the term genetic clusters is used interchangeably with the term genotypes. Within genogroup I, there are 8 GI clusters known to date (with prototype virus strain name): GI.1 (Norwalk (NV-USA93)); GI.2 (Southhampton (SOV-GBR93)); GI.3 (Desert Shield (DSV-USA93)); GI.4 (Cruise Ship virus/Chiba (Chiba-JPN00)); GI.5 (318/Musgrove (Musgrov-GBR00)); GI.6 (Hesse (Hesse-DEU98)); GI.7 (Wnchest-GBR00); and GI.8 (Boxer-USA02). Within genogroup II, there are 19 GII clusters known to date (with prototype virus strain name): GII.1 (Hawaii (Hawaii-USA94)); GII.2 (Snow Mountain/Melksham (Msham-GBR95)); GII.3 (Toronto (Toronto-CAN93)); GII.4 (Bristol/Lordsdale (Bristol-GBR93)); GII.5 (290/Hillingdon (Hilingd-GBR00)); GII.6 (269/Seacroft (Seacrof-GBR00)); GII.7 (273/Leeds (Leeds-GBR00)); GII.8 (539/Amsterdam (Amstdam-NLD99)); GII.9 (378 (VABeach-USA01)), GII.10 (Erfurt-DEU01); GII.11 (SW9180JPN01); GII.12 (Wortley-GBR00); GII.13 (Faytvil-USA02); GII.14 (M7-USA03); GII.15 (J23-USA02); GII.16 (Tiffin-USA03); GII.17 (CSE1-USA03); GII.18 (QW101/2003/US) and GII.19 (QW170/2003/US). In one embodiment, the capsid protein is derived from a Genogroup I or Genogroup II Norovirus. In another embodiment, the capsid protein is derived from a Genogroup I, genotype 1 (GI.1) or Genogroup II, genotype 4 (GII.4) Norovirus.

Preferably, the Norovirus capsid protein incorporated into the chimeric proteins of the invention is VP1, the major capsid protein encoded by open reading frame (ORF) 2. In one embodiment, the capsid protein has an amino acid sequence of SEQ ID NO: 1. The capsid protein component of the novel chimeric proteins can be derived from the major capsid protein of any of the known Norovirus strains. See, for example, GenBank entries: Norovirus genogroup 1 strain Hu/NoV/West Chester/2001/USA, GenBank Accession No. AY502016; Norovirus genogroup 2 strain Hu/NoV/Braddock Heights/1999/USA, GenBank Accession No. AY502015; Norovirus genogroup 2 strain Hu/NoV/Fayette/1999/USA, GenBank Accession No. AY502014; Norovirus genogroup 2 strain Hu/NoV/Fairfield/1999/USA, GenBank Accession No. AY502013; Norovirus genogroup 2 strain Hu/NoV/Sandusky/1999/USA, GenBank Accession No. AY502012; Norovirus genogroup 2 strain Hu/NoV/Canton/1999/USA, GenBank Accession No. AY502011; Norovirus genogroup 2 strain Hu/NoV/Tiffin/1999/USA, GenBank Accession No. AY502010; Norovirus genogroup 2 strain Hu/NoV/CS-E1/2002/USA, GenBank Accession No. AY50200; Norovirus genogroup 1 strain Hu/NoV/Wisconsin/2001/USA, GenBank Accession No. AY502008; Norovirus genogroup 1 strain Hu/NoV/CS-841/2001/USA, GenBank Accession No. AY502007; Norovirus genogroup 2 strain Hu/NoV/Hiram/2000/USA, GenBank Accession No. AY502006; Norovirus genogroup 2 strain Hu/NoV/Tontogany/1999/USA, GenBank Accession No. AY502005; Norwalk virus, complete genome, GenBank Accession No. NC.sub.—001959; Norovirus Hu/GI/Otofuke/1979/JP genomic RNA, complete genome, GenBank Accession No. AB187514; Norovirus Hu/Hokkaido/133/2003/JP, GenBank Accession No. AB212306; Norovirus Sydney 2212, GenBank Accession No. AY588132; Norwalk virus strain SN2000JA, GenBank Accession No. AB190457; Lordsdale virus complete genome, GenBank Accession No. X86557; Norwalk-like virus genomic RNA, Gifu'96, GenBank Accession No. AB045603; Norwalk virus strain Vietnam 026, complete genome, GenBank Accession No. AF504671; Norovirus Hu/GII.4/2004/N/L, GenBank Accession No. AY883096; Norovirus Hu/GII/Hokushin/03/JP, GenBank Accession No. AB 195227; Norovirus Hu/GII/Kamo/03/JP, GenBank Accession No. AB195228; Norovirus Hu/GII/Sinsiro/97/JP, GenBank Accession No. AB195226; Norovirus Hu/GII/Ina/02/JP, GenBank Accession No. AB 195225; Norovirus Hu/NLV/GII/Neustrelitz260/2000/DE, GenBank Accession No. AY772730; Norovirus Hu/NLV/Dresden174/pUS-NorII/1997/GE, GenBank Accession No. AY741811; Norovirus Hu/NLV/Oxford/B2S16/2002/UK, GenBank Accession No. AY587989; Norovirus Hu/NLV/Oxford/B4S7/2002/UK, GenBank Accession No. AY587987; Norovirus Hu/NLV/Witney/B7S2/2003/UK, GenBank Accession No. AY588030; Norovirus Hu/NLV/Banbury/B9S23/2003/UK, GenBank Accession No. AY588029; Norovirus Hu/NLV/ChippingNorton/2003/UK, GenBank Accession No. AY588028; Norovirus Hu/NLV/Didcot/B9S2/2003/UK, GenBank Accession No. AY588027; Norovirus Hu/NLV/Oxford/B8S5/2002/UK, GenBank Accession No. AY588026; Norovirus Hu/NLV/Oxford/B6S4/2003/UK, GenBank Accession No. AY588025; Norovirus Hu/NLV/Oxford/B6S5/2003/UK, GenBank Accession No. AY588024; Norovirus Hu/NLV/Oxford/B5S23/2003/UK, GenBank Accession No. AY588023; Norovirus Hu/NLV/Oxford/B6S2/2003/UK, GenBank Accession No. AY588022; Norovirus Hu/NLV/Oxford/B6S6/2003/UK, GenBank Accession No. AY588021; Norwalk-like virus isolate Bo/Thirsk10/00/UK, GenBank Accession No. AY126468; Norwalk-like virus isolate Bo/Penrith55/00/UK, GenBank Accession No. AY126476; Norwalk-like virus isolate Bo/Aberystwyth24/00/UK, GenBank Accession No. AY126475; Norwalk-like virus isolate Bo/Dumfries/94/UK, GenBank Accession No. AY126474; Norovirus NLV/IF2036/2003/Iraq, GenBank Accession No. AY675555; Norovirus NLV/IF1998/2003/Iraq, GenBank Accession No. AY675554; Norovirus NLV/BUDS/2002/USA, GenBank Accession No. AY660568; Norovirus NLV/Paris Island/2003/USA, GenBank Accession No. AY652979; Snow Mountain virus, complete genome, GenBank Accession No. AY134748; Norwalk-like virus NLV/Fort Lauderdale/560/1998/US, GenBank Accession No. AF414426; Hu/Norovirus/hiroshima/1999/JP (9912-02F), GenBank Accession No. AB044366; Norwalk-like virus strain 11MSU-MW, GenBank Accession No. AY274820; Norwalk-like virus strain B-1SVD, GenBank Accession No. AY274819; Norovirus genogroup 2 strain Hu/NoV/Farmington Hills/2002/USA, GenBank Accession No. AY502023; Norovirus genogroup 2 strain Hu/NoV/CS-G4/2002/USA, GenBank Accession No. AY502022; Norovirus genogroup 2 strain Hu/NoV/CS-G2/2002/USA, GenBank Accession No. AY502021; Norovirus genogroup 2 strain Hu/NoV/CS-G12002/USA, GenBank Accession No. AY502020; Norovirus genogroup 2 strain Hu/NoV/Anchorage/2002/USA, GenBank Accession No. AY502019; Norovirus genogroup 2 strain Hu/NoV/CS-D1/2002/CAN, GenBank Accession No. AY502018; Norovirus genogroup 2 strain Hu/NoV/Gennanton/2002/USA, GenBank Accession No. AY502017; Human calicivirus NLV/GII/Langen1061/2002/DE, complete genome, GenBank Accession No. AY485642; Murine norovirus 1 polyprotein, GenBank Accession No. AY228235; Norwalk virus, GenBank Accession No. AB067536; Human calicivirus NLV/Mex7076/1999, GenBank Accession No. AF542090; Human calicivirus NLV/Oberhausen 455/01/DE, GenBank Accession No. AF539440; Human calicivirus NLV/Herzberg 385/01/DE, GenBank Accession No. AF539439; Human calicivirus NLV/Boxer/2001/US, GenBank Accession No. AF538679; Norwalk-like virus genomic RNA, complete genome, GenBank Accession No. AB081723; Norwalk-like virus genomic RNA, complete genome, isolate:Saitama U201, GenBank Accession No. AB039782; Norwalk-like virus genomic RNA, complete genome, isolate:Saitama U18, GenBank Accession No. AB039781; Norwalk-like virus genomic RNA, complete genome, isolate:Saitama U25, GenBank Accession No. AB039780; Norwalk virus strain:U25GII, GenBank Accession No. AB067543; Norwalk virus strain: U201 GII, GenBank Accession No. AB067542; Norwalk-like viruses strain 416/97003156/1996/LA, GenBank Accession No. AF080559; Norwalk-like viruses strain 408/97003012/1996/FL, GenBank Accession No. AF080558; Norwalk-like virus NLV/Burwash Landing/331/1995/US, GenBank Accession No. AF414425; Norwalk-like virus NLV/Miami Beach/326/1995/US, GenBank Accession No. AF414424; Norwalk-like virus NLV/White River/290/1994/US, GenBank Accession No. AF414423; Norwalk-like virus NLV/New Orleans/306/1994/US, GenBank Accession No. AF414422; Norwalk-like virus NLV/Port Canaveral/301/1994/US, GenBank Accession No. AF414421; Norwalk-like virus NLV/Honolulu/314/1994/US, GenBank Accession No. AF414420; Norwalk-like virus NLV/Richmond/283/1994/US, GenBank Accession No. AF414419; Norwalk-like virus NLV/Westover/302/1994/US, GenBank Accession No. AF414418; Norwalk-like virus NLV/UK3-17/12700/1992/GB, GenBank Accession No. AF414417; Norwalk-like virus NLV/Miami/81/1986/US, GenBank Accession No. AF414416; Snow Mountain strain, GenBank Accession No. U70059; Desert Shield virus DSV395, GenBank Accession No. U04469; Norwalk virus, complete genome, GenBank Accession No. AF093797; Hawaii calicivirus, GenBank Accession No. U07611; Southampton virus, GenBank Accession No. L07418; Norwalk virus (SRSV-KY-89/89/J), GenBank Accession No. L23828; Norwalk virus (SRSV-SMA/76/US), GenBank Accession No. L23831; Camberwell virus, GenBank Accession No. U46500; Human calicivirus strain Melksham, GenBank Accession No. X81879; Human calicivirus strain MX, GenBank Accession No. U22498; Minireovirus TV24, GenBank Accession No. U02030; and Norwalk-like virus NLV/Gwynedd/273/1994/US, GenBank Accession No. AF414409; sequences of all of which (as entered by the date of filing of this application) are herein incorporated by reference. Additional Norovirus sequences are disclosed in the following patent publications: WO 2005/030806, WO 2000/79280, JP2002020399, US2003129588, U.S. Pat. No. 6,572,862, WO 1994/05700, and WO 05/032457, all of which are herein incorporated by reference in their entireties. See also Green et al. (2000) J. Infect. Dis., Vol. 181(Suppl. 2):S322-330; Wang et al. (1994) J. Virol., Vol. 68:5982-5990; Chen et al. (2004) J. Virol., Vol. 78: 6469-6479; Chakravarty et al. (2005) J. Virol., Vol. 79: 554-568; Hansman et al. (2006) J. Gen. Virol., Vol. 87:909-919; Bull et al. (2006) J. Clin. Micro., Vol. 44(2):327-333; Siebenga, et al. (2007) J. Virol., Vol. 81(18):9932-9941; and Fankhauser et al. (1998) J. Infect. Dis., Vol. 178:1571-1578; for sequence comparisons and a discussion of genetic diversity and phylogenetic analysis of Noroviruses.

In other embodiments, the capsid protein component of the chimeric proteins is a composite capsid protein derived from two or more circulating strains of Norovirus. Composite capsid protein sequences that incorporate amino acid sequences from two or more circulating Norovirus strains are described in International Application No. PCT/US2009/053249, filed Aug. 10, 2009, which is herein incorporated by reference. In one embodiment, the composite capsid protein is derived from two or more circulating strains of Genogroup II.4 Norovirus. In one particular embodiment, the composite capsid protein has an amino acid sequence of SEQ ID NO: 2.

In certain embodiments, the chimeric proteins of the invention comprise a capsid protein derived from a Sapovirus. The Sapovirus genus can be further categorized into five different genogroups (GI-GV). The capsid protein can be derived from a VP1 capsid protein of a Sapovirus in any of the five genogroups. For instance, in some embodiments, the capsid protein is derived from a capsid protein of Sapporo virus, London/29845 virus, Hu/Yokohamal 6-4/2007/JP virus, Manchester virus, Houston/86 virus, Houston/90 virus, and Parkville virus. In one particular embodiment, the capsid protein has an amino acid sequence of SEQ ID NO: 3. The capsid protein component of the novel chimeric proteins can be derived from the major capsid protein of any of the known Sapovirus strains. For example, GenBank entries: Sapovirus Mc10, GenBank Accession No. NC.sub.—010624; Sapporo virus, GenBank Accession No. U65427; Sapovirus Mc10, GenBank Accession No. AY237420; Sapovirus SaKaeo-15/Thailand, GenBank Accession No. AY646855; Sapporo virus, GenBank Accession No. NC.sub.—006269; Sapovirus C12, GenBank Accession No. NC.sub.—006554; Sapovirus C12, GenBank Accession No. AY603425; Sapovirus Hu/Dresden/pJG-Sap01/DE, GenBank Accession No. AY694184; Human calicivirus SLV/cruise ship/2000/USA, GenBank Accession No. AY289804; Human calicivirus SLV/Arg39, GenBank Accession No. AY289803; Porcine enteric calicivirus strain LL14, GenBank Accession No. AY425671; Porcine enteric calicivirus, GenBank Accession No. NC.sub.—000940; Human calicivirus strain Mc37, GenBank Accession No. AY237415; Mink enteric calicivirus strain Canada 151A, GenBank Accession No. AY144337; Human calicivirus SLV/Hou7-1181, GenBank Accession No. AF435814; Human calicivirus SLV/Mex 14917/2000, GenBank Accession No. AF435813; Human calicivirus SLV/Mex340/1990, GenBank Accession No. AF435812; Porcine enteric calicivirus, GenBank Accession No. AF182760; Sapporo virus-London/29845, GenBank Accession No. U95645; Sapporo virus-Manchester, GenBank Accession No. X86560; Sapporo virus-Houston/86, GenBank Accession No. U95643; Sapporo virus-Houston/90, GenBank Accession No. U95644; and Human calicivirus strain HuCV/Potsdam/2000/DEU, GenBank Accession No. AF294739; sequences of all of which (as entered by the date of filing of this application) are herein incorporated by reference. See also Schuffenecker et al. (2001) Arch Virol., Vol. 146(11): 2115-2132; Zintz et al. (2005) Infect. Genet. Evol., Vol. 5:281-290; Farkas et al. (2004) Arch. Virol., Vol. 149:1309-1323; for sequence comparisons and a discussion of genetic diversity and phylogenetic analysis of Sapoviruses.

The major capsid proteins of Caliciviruses are organized into distinct domains: the shell or "S" domain, and the protruding domain or "P" domain, which is further segregated into the P1 and P2 domains. The "S" domains of the capsid monomers coalesce to form the shell of the viral coat, while the stem-like P1 domain and the globular P2 domain project outward from the shell in arch-like structures. See Prasad et al. (2000) Journal of Infectious Diseases, Vol. 181: S317-S321 for characterization of Calicivirus structure. The P2 globular domain is located on the surface of the viral capsid and is thought to contain antigenic determinants and dictate host specificity (see, e.g., Crisci et al. (2009) Virology, Vol. 387: 303-312; Kumar et al. (2007) Journal of Virology, Vol. 81: 1119-1128; Katpally et al. (2008) Journal of Virology, Vol. 82: 2079-2088). The P1 domain and portions of the P2 domain are required to stabilize the capsid structure. The present inventors have identified particular solvent-exposed loop regions of the P2 domain (see Example 1) in which amino acid sequences from heterologous antigens can be inserted without disrupting the capsid structure. Thus, in one embodiment, at least one heterologous antigen or fragment thereof is inserted into the P2 domain of a Calicivirus capsid protein to form the chimeric proteins of the invention. In some embodiments, at least one heterologous antigen or fragment thereof is inserted into at least one solvent-exposed loop of the P2 domain of the Calicivirus capsid. As used herein, "solvent-exposed" or "solvent-accessible" refers to amino acid residues that are located on the exterior surface of the capsid monomer (rather than the hydrophobic core, VLP interior, or a protein-protein interface), when the monomer is folded into its native conformation in an assembled VLP. The present inventors employed sequence alignments, 3D structure analysis and 3D structure modeling as described herein to identify the P2 domain as well as the solvent-exposed loop domains in Calicivirus capsid proteins (see Example 1). Similar methods and software applications, such as Geno3D2 and Swiss PDB viewer, can be used according to the present invention to identify other suitable solvent-exposed loop residues in capsid proteins.

In certain embodiments, suitable solvent-exposed loops in a Norovirus capsid protein in which heterologous antigens or fragments thereof can be inserted include, but are not limited to, amino acids 293-300 of SEQ ID NO: 1, amino acids 305-313 of SEQ ID NO: 1, amino acids 335-342 of SEQ ID NO: 1, amino acids 348-351 of SEQ ID NO: 1, amino acids 362-368 of SEQ ID NO: 1, amino acids 380-386 of SEQ ID NO: 1, amino acids 397-405 of SEQ ID NO: 1, amino acids 293-300 of SEQ ID NO: 2, amino acids 306-317 of SEQ ID NO: 2, amino acids 338-346 of SEQ ID NO: 2, amino acids 354-357 of SEQ ID NO: 2, amino acids 366-375 of SEQ ID NO: 2, and amino acid of 388-405 of SEQ ID NO: 2 (see, e.g., underlined, bold regions in FIGS. 1A and B). In other embodiments, suitable solvent-exposed loops in a Sapovirus capsid protein in which heterologous antigens or fragments thereof can be inserted include, but are not limited to, amino acids 296-315 of SEQ ID NO: 3, amino acids 327-334 of SEQ ID NO: 3, amino acids 355-363 of SEQ ID NO: 3, amino acids 374-377 of SEQ ID NO: 3, amino acids 388-394 of SEQ ID NO: 3, amino acids 404-410 of SEQ ID NO: 3, amino acids 414-429 of SEQ ID NO: 3, amino acids 281-297 of SEQ ID NO: 3, amino acids 304-307 of SEQ ID NO: 3, amino acids 313-317 of SEQ ID NO: 3, amino acids 327-339 of SEQ ID NO: 3, amino acids 349-354 of SEQ ID NO: 3, amino acids 365-389 of SEQ ID NO: 3, amino acids 396-402 of SEQ ID NO: 3, and amino acids 421-424 of SEQ ID NO: 3 (see, e.g., underlined, bold regions in FIGS. 4A and B). One or more heterologous antigens or fragments thereof can be inserted into or replace one or more or all of the amino acids in a solvent-exposed loop.

One or more heterologous antigens or fragments thereof can be inserted into multiple solvent-exposed loops of the P2 domain, such as two, three, four, five, six, or seven solvent-exposed loops of the P2 domain. Multiple copies of the same heterologous antigen sequence may be inserted into the various solvent-exposed loops. Additionally or alternatively, different heterologous antigen sequences can be inserted into the different solvent-exposed loops to create a chimeric protein containing peptide sequences from a plurality of organisms, a plurality of proteins from one or more organisms, or a plurality of regions from one or more proteins.

In some embodiments, to form the chimeric proteins of the invention, amino acid sequences of heterologous antigens or peptides are directly inserted into a Calicivirus capsid sequence without deletion of capsid amino acid residues. Preferably, the heterologous amino acid sequences are directly fused within a solvent-exposed loop region of the P2 domain. In certain embodiments, at least one heterologous antigen sequence is inserted into a GI.1 Norwalk VP1 capsid sequence (SEQ ID NO: 1). Preferred insertion sites of heterologous antigen sequences into the Norwalk VP1 capsid sequence include insertions directly after the asparagine residue at position 295, the glycine residue at position 296, the proline residue at position 308, the glycine residue at position 336, the serine residue at position 338, the asparagine residue at position 362, the glycine residue at position 363, the proline residue at position 382, the serine residue at position 383, the isoleucine residue at position 399, or the alanine residue at position 402 of SEQ ID NO: 1.

In other embodiments, amino acid sequences of heterologous antigens or peptides replace one or more amino acids of a Calicivirus capsid protein in the chimeric proteins of the invention. For instance, at least one heterologous antigen or fragment thereof replaces about 1 to about 50 amino acids, about 2 to about 40 amino acids, about 4 to about 20 amino acids, about 8 to about 15 amino acids, or about 10 to about 30 amino acids of the capsid protein. In one particular embodiment, at least one heterologous antigen or fragment thereof replaces about 5 amino acids of the capsid protein. In some embodiments, at least one heterologous antigen sequence replaces at least one amino acid of a Norwalk VP1 capsid sequence (SEQ ID NO: 1). In one embodiment, amino acids 337-341 of SEQ ID NO: 1 are replaced by a heterologous amino acid sequence. In other embodiments, amino acids 294-298, amino acids 307-311, amino acids 362-366, amino acids 381-385, or amino acids 401-405 of SEQ ID NO: 1 are replaced by a heterologous amino acid sequence. In some embodiments, the heterologous amino acid sequence replaces all amino acids in a solvent-exposed loop of the capsid protein.

The chimeric proteins of the invention comprise at least one heterologous antigen or fragment thereof fused, optionally through a linker sequence (e.g., about 1 to about 10 amino acids or more), to or within a capsid protein sequence. A "heterologous antigen" refers to an immunogenic protein or peptide from a species different than the species in which the capsid protein is derived.

In some embodiments, the heterologous antigen or fragment thereof comprises an antigenic epitope. An "antigenic epitope" refers to a three-dimensional structure that is recognized by antibodies or cells of the immune system. As used herein, an antigenic epitope includes T-cell and B-cell epitopes as well as antibody-binding epitopes. In one embodiment, the heterologous antigen or fragment thereof comprises a mimotope. A mimotope is a linear amino acid sequence that mimics the structure of an epitope and consequently, is recognized by antibodies that bind to the epitope. In another embodiment, the heterologous antigen or fragment thereof comprises a composite linear amino acids sequence representing a discontinuous epitope or a linear amino acid sequence that contains a portion of a discontinuous epitope.

For example, heterologous antigen sequences comprising portions of a discontinuous epitope can be inserted into adjacent solvent-exposed loop regions such that the inserted sequences contact each other to generate the discontinuous epitope. Antigenic epitopes and mimotopes are known in the art for common pathogenic agents. For instance, T-cell epitopes useful in the invention described herein may be the immunodominant T-cell epitope on the F protein of Respiratory Syncytial Virus (RSV) (Levely et al., (1991) Journal of Virology, Vol. 65: 3789-3796) or the nucleoprotein-specific cytotoxic T-cell epitopes from RSV (Venter et al. (2003) Journal of Virology, Vol. 77: 7319-7329). The skilled artisan can ascertain other suitable epitopes for insertion into the chimeric proteins of the invention using routine methods in the art including, but not limited to, epitope mapping using protein microarrays, ELISPOT assays, and ELISA assays, phage display analysis, and structural modeling of antigen/antibody complexes.

In certain embodiments, multiple epitopes can be inserted into the chimeric proteins of the invention to provide one or more epitope libraries for subsequent screening.

In another embodiment, the foreign sequence inserted in the Calicivirus capsid protein comprises a high-affinity binding site for a particular foreign antigen. For this approach, recognition of the high-affinity binding site can be an inherent property of the foreign antigen or a construct can be generated where the foreign antigen is fused to a protein that recognizes the high-affinity binding site. For instance, the high-affinity binding site can be a paratrope or antigen-binding site of an antibody that binds to the foreign antigen or it can be a binding region of a protein that interacts with the foreign antigen, such as a receptor. In some embodiments, the high affinity binding site can be a short, linear binding motif such as a polyproline motif (recognized by SH2 domains), a leucine zipper (recognized by a binding partner that also contains a leucine zipper motif) or an eptiope (recognized by an antigen binding site of an antibody fragment). In such embodiments, foreign antigen is attached to a binding site that recognizes the short, linear peptide binding motif (engineered into the VP1 subunit) and is bound non-covalently to virus-like particles comprising the chimeric protein containing the foreign antigen binding site.

The heterologous antigen or fragment thereof can be of any length, more particularly from about 5 to about 70 amino acids in length, from about 8 to about 50 amino acids in length, from about 10 to about 40 amino acids in length, from about 15 to about 35 amino acids in length, or from about 20 to about 30 amino acids in length. In some embodiments, the heterologous antigen or fragment thereof is from about 5 to about 20 amino acids in length. The heterologous antigen or fragment thereof can be fused to the Calicivirus capsid sequence through an optional linker sequence. The linker sequence can be from about 1 to about 10 amino acids or more.

The heterologous antigen or fragment thereof can be derived from various pathogenic agents, such as viruses, bacteria, and eukaryotic pathogens. For example, in one embodiment, the heterologous antigen is derived from a virus. Viruses from which heterologous antigens can be derived include Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis, including Norwalk and related viruses); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus, metaneumovirus); Orthomyxoviridae (e.g. influenza viruses); Bungaviridae (e.g. Hantaan viruses, bunga viruses, phleboviruses and Nairo viruses); Arenaviridae (hemorrhagic fever viruses); Reoviridae (e.g. reoviruses, orbiviurses and rotaviruses); Bimaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g. the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e. Hepatitis C); and astroviruses. In certain embodiments, the virus is selected from the group consisting of rotavirus, respiratory syncytial virus, parainfluenza virus, and metaneumovirus. For example, target sequences such as $^{260}$LINDMPITN$^{268}$ (SEQ ID NO: 6) or $^{250}$YMLTNSELLSLINDMPITNDQKKLMSNNV$^{278}$ (SEQ ID NO: 7) derived from the respiratory syncytial virus F protein can be used to generate chimeric Calicivirus VLPs. In other embodiments, the virus is a Calicivirus. For instance, the heterologous antigen can be derived from any of the strains of Calicivirus described herein.

In some embodiments, the heterologous antigen is derived from a bacterial pathogen. Bacteria from which heterologous antigens can be derived include pathogenic *Pasteurella* species (e.g., *Pasteurella multocida*), Staphylococci species (e.g., *Staphylococcus aureus*), Streptococcus species (e.g., *Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus pneumoniae*), *Neisseria* species (e.g., *Neisseria gonorrhoeae, Neisseria meningitidis*), *Escherichia* species (e.g., enterotoxigenic *E. coli* (ETEC), enteropathogenic *E. coli* (EPEC), enterohemorrhagic *E. coli* (EHEC), and enteroinvasive *E. coli* (EIEC)), *Bordetella* species, *Campylobacter* species, *Legionella* species (e.g., *Legionella pneumophila*), *Pseudomonas* species, *Shigella* species, *Vibrio* species, *Yersinia* species, *Salmonella* species, *Haemophilus* species (e.g., *Haemophilus influenzae*), *Brucella* species, *Francisella* species, Bacterioides species, Clostridia species (e.g., *Clostridium difficile, Clostridium perfringens, Clostridium tetani*), *Mycobacteria* species (e.g. *M. tuberculosis, M. avium, M. intracellulare, M. kansaii, M. gordonae*), *Helicobacter pyloris, Borelia burgdorferi, Listeria monocytogenes, Chlamydia trachomatis, Enterococcus* species, *Bacillus anthracis, Corynebacterium diphtheriae, Erysipelothrix rhusiopathiae, Enterobacter aerogenes, Klebsiella pneumoniae, Fusobacterium nucleatum, Streptobacillus moniliformis, Treponema pallidium, Treponema pertenue, Leptospira, Rickettsia*, and *Actinomyces israeli*.

In other embodiments of the invention, the heterologous antigen or fragment thereof is derived from a eukaryotic pathogen, such as pathogenic fungi and parasites. Fungi from which the heterologous antigen can be derived include, but are not limited to, *Cryptococcus neoformans, Histoplasma capsulatum, Coccidioides immitis, Blastomyces dermatitidis, Candida albicans, Candida glabrata, Aspergillus fumigata,*

*Aspergillus flavus*, and *Sporothrix schenckii*. Other eukaryotic pathogens from which the heterologous antigen can be derived include pathogenic protozoa, helminths, *Plasmodium*, such as *Plasmodium falciparum, Plasmodium malariae, Plasmodium ovale*, and *Plasmodium vivax; Toxoplasma gondii; Trypanosoma brucei, Trypanosoma cruzi; Schistosoma haematobium, Schistosoma mansoni, Schistosoma japonicum; Leishmania donovani; Giardia intestinalis; Cryptosporidium parvum*; and the like.

In certain embodiments of the invention, the heterologous antigen or fragment thereof is derived from a tumor-associated antigen (TAA). Any of a variety of known tumor-specific antigens or tumor-associated antigens (TAA) can be used as one or more heterologous antigens or fragments thereof to be incorporated into a chimeric protein of the invention (Hirohashi, et al. (2009) Cancer Sci., Vol. 100(5):798-806). Tumor-associated antigens (or epitope-containing fragments thereof) which may be used in a chimeric protein of the invention include, but are not limited to, MAGE-2, MAGE-3, MUC-1, MUC-2, HER-2, high molecular weight melanoma-associated antigen MAA, GD2, carcinoembryonic antigen (CEA), TAG-72, ovarian-associated antigens OV-TL3 and MOV 18, TUAN, alpha-fetoprotein (AFP), OFP, CA-125, CA-50, CA-19-9, renal tumor-associated antigen G250, EGP-40 (also known as EpCAM), S100 (malignant melanoma-associated antigen), p53, and p21ras. A synthetic analog of any TAA (or epitope thereof), including any of the foregoing, may be used.

In another embodiment, the heterologous antigen or fragment thereof is derived from an allergen. Allergens from which one or more heterologous antigens or fragments thereof can be derived include, but are not limited to, environmental aeroallergens; plant pollens such as ragweed/hayfever; weed pollen allergens; grass pollen allergens; Johnson grass; tree pollen allergens; ryegrass; arachnid allergens, such as house dust mite allergens (e.g., Der p I, Der f I, etc.); storage mite allergens; Japanese cedar pollen/hay fever; mold spore allergens; animal allergens (e.g., dog, guinea pig, hamster, gerbil, rat, mouse, etc., allergens); food allergens (e.g., allergens of crustaceans; nuts, such as peanuts; citrus fruits); insect allergens; venoms: (Hymenoptera, yellow jacket, honey bee, wasp, hornet, fire ant); other environmental insect allergens from cockroaches, fleas, mosquitoes, etc.; bacterial allergens such as streptococcal antigens; parasite allergens such as Ascaris antigen; viral antigens; fungal spores; drug allergens; antibiotics; penicillins and related compounds; other antibiotics; whole proteins such as hormones (insulin), enzymes (streptokinase); occupational allergens such as flour (e.g., allergens causing Baker's asthma), castor bean, coffee bean; flea allergens; and human proteins in non-human animals. Examples of specific natural, animal and plant allergens include but are not limited to proteins specific to the following genuses: Canine (*Canis familiaris*); *Dermatophagoides* (e.g. *Dermatophagoides farinae*); *Felis* (*Felis domesticus*); *Ambrosia* (*Ambrosia artemiisfolia*); *Lolium* (e.g. *Lolium perenne* or *Lolium multiflorum*); *Cryptomeria* (*Cryptomeria japonica*); *Alternaria* (*Alternaria alternata*); Alder; *Alnus* (*Alnus gultinoas*); *Betula* (*Betula verrucosa*); *Quercus* (*Quercus alba*); *Olea* (*Olea europa*); *Artemisia* (*Artemisia vulgaris*); *Plantago* (e.g. *Plantago lanceolata*); *Parietaria* (e.g. *Parietaria officinalis* or *Parietaria judaica*); *Blattella* (e.g. *Blattella germanica*); *Apis* (e.g. *Apis multiflorum*); *Cupressus* (e.g. *Cupressus sempervirens, Cupressus arizonica* and *Cupressus macrocarpa*); *Juniperus* (e.g. *Juniperus sabinoides, Juniperus virginiana, Juniperus communis* and *Juniperus ashei*); *Thuya* (e.g. *Thuya orientalis*); *Chamaecyparis* (e.g. *Chamaecyparis obtusa*); *Periplaneta* (e.g. *Periplaneta americana*); *Agropyron* (e.g. *Agropyron repens*); *Secale* (e.g. *Secale cereale*); *Triticum* (e.g. *Triticum aestivum*); *Dactylis* (e.g. *Dactylis glomerata*); *Festuca* (e.g. *Festuca elatior*); *Poa* (e.g. *Poa pratensis* or *Poa compressa*); *Avena* (e.g. *Avena sativa*); *Holcus* (e.g. *Holcus lanatus*); *Anthoxanthum* (e.g. *Anthoxanthum odomtum*); *Arrhenatherum* (e.g. *Arrhenatherum elatius*); *Agrostis* (e.g. *Agrostis alba*); *Phleum* (e.g. *Phleum pratense*); *Phalaris* (e.g. *Phalaris arundinacea*); *Paspalum* (e.g. *Paspalum notatum*); *Sorghum* (e.g. *Sorghum halepensis*); and *Bromus* (e.g. *Bromus inermis*).

The present invention includes isolated nucleic acids and vectors encoding chimeric proteins as described herein. In one embodiment, the isolated nucleic acid encodes a chimeric protein comprising a Calicivirus capsid protein having a P2 domain and at least one heterologous antigen or fragment thereof, wherein said at least one heterologous antigen or fragment thereof is inserted into said P2 domain of said capsid protein. In another embodiment, the invention provides a vector comprising an isolated nucleic acid encoding a chimeric protein as described herein. In yet another embodiment, the invention provides a host cell comprising a vector encoding a chimeric protein of the invention. The host cell can be a bacterial cell, an insect cell, a yeast cell, or a mammalian cell.

The chimeric proteins of the present invention and isolated nucleic acids encoding the same can be prepared by routine methods known in the art. Capsid proteins can be prepared by isolation and purification from the particular Calicivirus in which they occur naturally, or they may be prepared by recombinant techniques. Once coding sequences for the desired particle-forming polypeptides have been isolated or synthesized, they can be cloned into any suitable vector or replicon for expression. Numerous cloning/expression vectors are known to those of skill in the art, and the selection of an appropriate cloning/expression vector is within the skill of an ordinary artisan. One or more heterologous antigen sequences can be inserted into the designated locations within the Calicivirus capsid protein sequence using routine technologies and molecular biological methods, including DNA synthesis, PCR mutagenesis, and restriction endonuclease digestion followed by DNA ligation.

General texts which describe molecular biological techniques, which are applicable to the present invention, such as cloning, mutation, and the like, include Berger and Kimmel, Guide to Molecular Cloning Techniques, Methods in Enzymology volume 152 Academic Press, Inc., San Diego, Calif. (Berger); Sambrook et al., Molecular Cloning—A Laboratory Manual (3rd Ed.), Vol. 1-3, Cold Spring Harbor Laboratory, Cold Spring Harbor, N.Y., 2000 ("Sambrook") and Current Protocols in Molecular Biology, F. M. Ausubel et al., eds., Current Protocols, a joint venture between Greene Publishing Associates, Inc. and John Wiley & Sons, Inc., ("Ausubel"). These texts describe mutagenesis, the use of vectors, promoters and many other relevant topics related to, e.g., the cloning and expression of chimeric capsid proteins.

The chimeric proteins of the invention are capable of forming virus-like particles (VLPs) when expressed in a host cell. Thus, the present invention also includes a virus-like particle comprising a chimeric protein as described herein. The inventors have discovered a unique strategy for engineering capsid protein sequences of Calicivirus to incorporate heterologous amino acid sequences, while preserving the ability of the capsid protein to form VLPs. In some embodiments, the chimeric protein is co-expressed with one or more structural proteins from a Calicivirus, such as the minor capsid protein VP2. The additional structural proteins can be from the same Calicivirus from which the chimeric protein is derived or they can be from a different Calicivirus.

In certain embodiments, VLPs comprise a chimeric protein of the invention and a native capsid protein from a Calicivirus. Solely by way of example, the VLP can comprise a chimeric protein and a Norwalk VP1 capsid protein. The ratio of chimeric protein to native capsid protein in the VLP can be adjusted to enhance VLP formation. For instance, the ratio of chimeric protein to native capsid protein can be from about 1:10 to about 10:1, from about 1:5 to about 5:1, or about 1:1. VLPs containing a mixture of chimeric and native capsid proteins can be generated by expressing each of the capsid proteins (i.e. chimeric and native) separately, purifying the proteins, and mixing the two purified capsid proteins in the desired ratio to form the mixed VLPs. Alternatively, the chimeric and native capsid proteins can be co-expressed in a host cell from two different promoters. Use of different strength promoters allows for the control of the ratio of chimeric protein to native capsid protein in the resulting VLPs.

In another embodiment, the chimeric proteins of the invention can be further modified to enhance VLP formation. For instance, the solvent-exposed loop regions of the capsid amino acid sequence and/or the heterologous antigen amino acid sequence can be engineered to contain one or more motifs to control the conformation of the chimeric protein. Such stabilizing motifs could be designed to drive desired protein contacts through mechanisms including ionic interactions (such as salt bridges), metal coordination (such as zinc finger), hydrophobic interactions (such as leucine zipper) or covalent interations (such as disulphide bond formation).

The present invention encompasses a method of making a chimeric VLP. In one embodiment, the method comprises expressing a chimeric protein of the invention in a host cell, and growing said host cell in conditions in which VLPs are formed. A vector encoding the chimeric protein sequence as described herein is used to transform an appropriate host cell. Suitable recombinant expression systems include, but are not limited to, bacterial (e.g. *E. coli, Bacillus subtilis*, and *Streptococcus*), baculovirus/insect, vaccinia, Semliki Forest virus (SFV), Alphaviruses (such as, Sindbis, Venezuelan Equine Encephalitis (VEE)), mammalian (e.g. Chinese hamster ovary (CHO) cells, HEK-293 cells, HeLa cells, baby hamster kidney (BHK) cells, mouse myeloma (SB20), and monkey kidney cells (COS)), yeast (e.g. *S. cerevisiae, S. pornbe, Pichia pastori* and other *Pichia* expression systems), plant, and *Xenopus* expression systems, as well as others known in the art. Particularly preferred expression systems are mammalian cell lines, bacteria, insect cells, and yeast expression systems. Cell-free transcription translation systems represent an additional method for production of chimeric VLPs.

In certain embodiments, the chimeric VLPs are prepared from insect cells such as *Aedes aegypti, Bombyx mori, Drosophila melanogaster, Spodoptera frugiperda* (Sf9), and *Trichoplusia ni* (e.g., High Five, TniPro). The procedures for producing VLPs in insect cell culture is well known in the art (see, for example, U.S. Pat. No. 6,942,865, which is incorporated herein by reference in its entirety). Briefly, the recombinant baculoviruses carrying the chimeric capsid sequence are constructed by inserting synthetic or cloned reading frames encoding the target gene. The recombinant baculovirus are then used to infect insect cell cultures (e.g. Sf9, High Five and TniPro cells) and chimeric VLPs can be isolated from the cell culture. A "chimeric VLP" is a VLP comprising at least one polypeptide having a chimeric amino acid sequence as described herein.

If the VLPs are formed intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990).

The particles are then isolated (or substantially purified) using methods that preserve the integrity thereof, such as, by density gradient centrifugation, e.g., sucrose gradients, PEG-precipitation, pelleting, and the like (see, e.g., Kirnbauer et al. J. Virol. (1993) 67:6929-6936), as well as standard purification techniques including chromatographic methods, e.g., ion exchange and gel filtration chromatography.

In some embodiments, the chimeric VLPs are produced in vivo by administration of a vector comprising an isolated nucleic acid encoding a chimeric protein. Suitable vectors include, but are not limited to, viral vectors, such as Vesicular Stomatitis Virus (VSV) vector, Equine Encephalitis Virus (EEV) vector, Poxvirus vector, Adenovirus vector, Adeno-Associated Virus (AAV), retrovirus vector, and expression plasmids, such as pFastBacl, pWINEO, pSV2CAT, pOG44, pXT1, pSG, pSVK3, pBPV, pMSG, and pSVL. Other suitable vectors will be readily apparent to the skilled artisan.

The present invention provides a vaccine formulation comprising one or more of the VLPs as described herein. In one embodiment, the vaccine formulation comprises a chimeric VLP, wherein said chimeric VLP comprises a chimeric protein containing a Calicivirus capsid protein having a P2 domain and at least one heterologous antigen or fragment thereof, wherein said at least one heterologous antigen or fragment thereof is inserted into said P2 domain of said capsid protein. In certain embodiments, the Calicivirus capsid protein in the chimeric protein is a Norovirus or Sapovirus capsid protein. In one particular embodiment, the chimeric protein comprises a capsid protein from a Norovirus Genogroup I or Genogroup II Norovirus. In another embodiment, the chimeric protein comprises a capsid protein from a GI.1 or GII.4 Norovirus.

In certain embodiments, the vaccine formulation comprising at least one chimeric VLP of the invention does not contain an adjuvant. In some embodiments, the vaccine formulation may further comprise an adjuvant. Most adjuvants contain a substance designed to protect the antigen from rapid catabolism, such as aluminum hydroxide or mineral oil, and a stimulator of immune responses, such as *Bordatella pertussis* or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); mineral salts, including aluminum salts such as aluminum hydroxide gel (alum) or aluminum phosphate and salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, monophosphoryl lipid A (MPL), synthetic lipid A, lipid A mimetics or analogs, aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsion, MF59, and squalene. In some embodiments, the adjuvants are bacterially-derived exotoxins. In other embodiments, adjuvants which stimulate a Th1 type response, such as 3DMPL or QS21, may be used. In certain embodiments, the adjuvant is a combination of MPL and aluminum hydroxide.

In certain embodiments, the adjuvant is monophosphoryl lipid A (MPL). MPL is a non-toxic derivative of lipid A from *Salmonella*, is a potent TLR-4 agonist that has been developed as a vaccine adjuvant (Evans et al. (2003) Expert Rev Vaccines, Vol. 2: 219-229). In pre-clinical murine studies intranasal MPL has been shown to enhance secretory, as well as systemic, humoral responses (Baldridge et al. (2000) Vaccine, Vol. 18: 2416-2425; Yang et al. (2002) Infect Immun., Vol. 70: 3557-3565). It has also been proven to be safe and effective as a vaccine adjuvant in clinical studies of greater than 120,000 patients (Baldrick et al. (2002) Regul Toxicol Pharmacol, Vol. 35: 398-413). MPL stimulates the induction of innate immunity through the TLR-4 receptor and is thus capable of eliciting nonspecific immune responses against a wide range of infectious pathogens, including both gram negative and gram positive bacteria, viruses, and parasites (Persing et al. (2002) Trends Microbiol, Vol. 10: S32-37). Inclusion of MPL in vaccine formulations should provide rapid induction of innate responses, eliciting nonspecific immune responses from viral challenge while enhancing the specific responses generated by the antigenic components of the vaccine. In some embodiments, MPL can be combined with one or more additional adjuvants. For instance, MPL can be combined with aluminum hydroxide to create a suitable adjuvant for intramuscular administration of a vaccine formulation.

In other embodiments, the adjuvant is a naturally occurring oil, such as squalene. Squalene is a triterpenoid hydrocarbon oil ($C_{30}H_{50}$) produced by plants and is present in many foods. Squalene is also produced abundantly by human beings, for whom it serves as a precursor of cholesterol and steroid hormones. It is synthesized in the liver and the skin, transported in the blood by very-low-density lipoproteins (VLDL) and low-density lipoproteins (LDL), and secreted in large amounts by sebaceous glands.

Since it is a natural component of the human body and is biodegradable, squalene has been used as a component of vaccine adjuvants. One of these squalene adjuvants is MF59, an oil-in-water emulsion developed by Chiron. MF59 has been shown in various preclinical and clinical studies to significantly enhance the immune response to a wide variety of vaccine antigens. MF59 is a part of an influenza subunit vaccine, which has been licensed in various European countries since 1997. More than 20 million doses of this vaccine have been given, and it has been shown to have an excellent safety profile. The safety of vaccines with the MF59 adjuvant has also been shown by various investigational clinical studies using recombinant antigens from hepatitis B virus, hepatitis C virus, cytomegalovirus, herpes simplex virus, human immunodeficiency virus, uropathogenic *Escherichia coli*, etc., in various age groups, including 1- to 3-day-old newborns.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation. Suitably effective increases in immunoglobulin levels include by more than 5%, preferably by more than 25%, and in particular by more than 50%, as compared to the same antigen composition without any adjuvant.

In another embodiment of the invention, the vaccine formulation may further comprise a delivery agent, which functions to enhance antigen uptake based upon, but not restricted to, increased fluid viscosity due to the single or combined effect of partial dehydration of host mucopolysaccharides, the physical properties of the delivery agent, or through ionic interactions between the delivery agent and host tissues at the site of exposure, which provides a depot effect. Alternatively, the delivery agent can increase antigen retention time at the site of delivery (e.g., delay expulsion of the antigen). Such a delivery agent may be a bioadhesive agent. In some embodiments, the bioadhesive may be a mucoadhesive agent selected from the group consisting of glycosaminoglycans (e.g., chondroitin sulfate, dermatan sulfate chondroitin, keratan sulfate, heparin, heparan sulfate, hyaluronan), carbohydrate polymers (e.g., pectin, alginate, glycogen, amylase, amylopectin, cellulose, chitin, stachyose, unulin, dextrin, dextran), crosslinked derivatives of poly(acrylic acid), polyvinyl alcohol, polyvinyl pyrollidone, polysaccharides (including mucin, other mucopolysaccharides, and GelSite®, a natural acidic polysaccharide extracted from the aloe plant), polyions, cellulose derivatives (e.g., hydroxypropyl methylcellulose, carboxymethylcellulose), proteins (e.g. lectins, fimbrial proteins), and deoxyribonucleic acid. In one embodiment, the vaccine formulations comprise a polysaccharide such as chitosan, chitosan salt, chitosan base, or a natural polysaccharide (e.g. GelSite®).

Chitosan, a positively charged linear polysaccharide derived from chitin in the shells of crustaceans, is a bioadhesive for epithelial cells and their overlaying mucus layer. Formulation of antigens with chitosan increases their contact time with the nasal membrane, thus increasing uptake by virtue of a depot effect (Illum et al. (2001) Adv Drug Deliv Rev, Vol. 51: 81-96; Illum et al. (2003) J Control Release, Vol. 87: 187-198; Davis et al. (1999) Pharm Sci Technol Today, Vol. 2: 450-456; Bacon et al. (2000) Infect Immun., Vol. 68: 5764-5770; van der Lubben et al. (2001) Adv Drug Deliv Rev, Vol. 52: 139-144; van der Lubben et al. (2001) Eur J Pharm Sci, Vol. 14: 201-207; Lim et al. (2001) AAPS Pharm Sci Tech, Vol. 2: 20). Chitosan has been tested as a nasal delivery system for several vaccines, including influenza, pertussis and diphtheria, in both animal models and humans (Illum et al. (2001) Adv Drug Deliv Rev, Vol. 51: 81-96; Illum et al. (2003) J Control Release, Vol. 87: 187-198; Bacon et al. (2000) Infect Immun., Vol. 68: 5764-5770; Jabbal-Gill et al. (1998) Vaccine, Vol. 16: 2039-2046; Mills et al. (2003) A Infect Immun, Vol. 71: 726-732; McNeela et al. (2004) Vaccine, Vol. 22: 909-914). In these trials, chitosan was shown to enhance systemic immune responses to levels equivalent to parenteral vaccination. In addition, significant antigen-specific IgA levels were also measured in mucosal secretions. Thus, chitosan can greatly enhance a nasal vaccine's effectiveness. Moreover, due to its physical characteristics, chitosan is particularly well suited to intranasal vaccines formulated as powders (van der Lubben et al. (2001) Eur J Pharm Sci, Vol. 14: 201-207; Mikszta et al. (2005) J Infect Dis, Vol. 191: 278-288; Huang et al. (2004) Vaccine, Vol. 23: 794-801).

In some embodiments of the present invention, among others, vaccine formulations comprise chitosan, a chitosan salt, or a chitosan base. The molecular weight of the chitosan may be between 10 kDa and 800 kDa, preferably between 100 kDa and 700 kDa and more preferably between 200 kDa and 600 kDa. The concentration of chitosan in the composition will typically be up to about 80% (w/w), for example, 5%, 10%, 30%, 50%, 70% or 80%. The chitosan is one which is preferably at least 75% deacetylated, for example 80-90%, more preferably 82-88% deacetylated, particular examples being 83%, 84%, 85%, 86% and 87% deacetylation.

The vaccine formulation may further comprise a pharmaceutically acceptable carrier. A pharmaceutically acceptable carrier, including any suitable diluent or excipient, includes any pharmaceutical agent that does not itself induce the production of an immune response harmful to the subject receiving the vaccine formulation, and which may be administered without undue toxicity. As used herein, the term "pharmaceutically acceptable" means being approved by a regulatory agency of the Federal or a state government or listed in the U.S. Pharmacopia, European Pharmacopia or other generally recognized pharmacopia for use in mammals, and more particularly in humans. Pharmaceutically acceptable carriers include, but are not limited to, saline, buffered saline, dextrose, water, glycerol, sterile isotonic aqueous buffer, and combinations thereof. A thorough discussion of pharmaceutically acceptable carriers, diluents, and other excipients is presented in Remington's Pharmaceutical Sciences (Mack Pub. Co. N.J. current edition). The formulation should suit the mode of administration. In a preferred embodiment, the formulation is suitable for administration to humans, preferably the formulation is sterile, non-particulate and/or non-pyrogenic. The vaccine formulation, if desired, can also contain minor amounts of wetting or emulsifying agents, or pH buffering agents.

The VLPs or chimeric proteins of the invention can be formulated for administration as vaccines or antigenic formulations. As used herein, the team. "vaccine" refers to a formulation which contains VLPs or chimeric proteins of the present invention as described above, which is in a form that is capable of being administered to a vertebrate (e.g., a mammal) and which induces a protective immune response sufficient to induce immunity to prevent and/or ameliorate an infection and/or to reduce at least one symptom of an infection and/or to enhance the efficacy of another dose of VLPs or chimeric protein. In some embodiments, the vaccine formulations do not contain an adjuvant. In other embodiments, the vaccine formulations may contain an adjuvant as described herein. As used herein, the term "antigenic formulation" or "antigenic composition" refers to a preparation which, when administered to a vertebrate, e.g. a mammal, will induce an immune response. As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-lymphocytes and/or other cells, such as macrophages, against an infectious agent, exhibited by a vertebrate (e.g., a human), that prevents or ameliorates infection or reduces at least one symptom thereof. In particular, "protective immunity" or "protective immune response" refers to immunity or eliciting an immune response against an infectious agent, which is exhibited by a vertebrate (e.g., a human), that prevents or ameliorates an infection or reduces at least one symptom thereof. Specifically, induction of a protective immune response from administration of the vaccine is evident by elimination or reduction of the presence of one or more symptoms associated with the pathogenic organism from which the heterologous antigen present in the chimeric protein is derived. Vaccine preparation is generally described in Vaccine Design ("The subunit and adjuvant approach" (eds Powell M. F. & Newman M. J.) (1995) Plenum Press New York). The compositions of the present invention can be formulated, for example, for administration to a subject by mucosal or parenteral (e.g. intramuscular, intravenous, subcutaneous, intradermal, subdermal, or transdermal) routes of administration. Such mucosal administration could be, but is not limited to, through gastro-intestinal, intranasal, oral, or vaginal delivery. In one embodiment, the vaccine formulation is in the form of a nasal spray, nasal drops or dry powder. In another embodiment, the vaccine formulation is in a form suitable for intramuscular administration.

Vaccine formulations of the invention may be liquid formulations or dry powder formulations. Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

In one embodiment, the vaccine formulation contains one or more chimeric VLPs as the immunogen, an adjuvant such as MPL®, squalene, or MF59®, a biopolymer such as chitosan or GelSite® to promote adhesion to mucosal surfaces, and bulking agents such as mannitol and sucrose.

For example, a vaccine may be formulated as 10 mg of a dry powder containing one or more chimeric VLPs as discussed herein, MPL® adjuvant, chitosan mucoadhesive, and mannitol and sucrose as bulking agents and to provide proper flow characteristics. The formulation may comprise about 7.0 mg (25 to 90% w/w range) chitosan, about 1.5 mg mannitol (0 to 50% w/w range), about 1.5 mg sucrose (0 to 50% w/w range), about 25 µg MPL® (0.1 to 5% w/w range), and about 100 µg chimeric VLP antigen (0.05 to 5% w/w range).

Chimeric VLPs/antigens may be present in a concentration of from about 0.01% (w/w) to about 80% (w/w). In one embodiment, VLPs can be formulated at dosages of about 5 µg, about 15 µg, about 25 µg, about 50 µg, about 75 µg, about 100 µg, about 150 µg, about 200 µg, about 500 µg, and about 1 mg per 10 mg dry powder formulation (0.05, 0.15, 0.25, 0.5, 1.0, 2.0, 5.0, and 10.0% w/w) for administration into both nostrils (10 mg per nostril) or about 10 µg, about 30 µg, about 50 µg, about 100 µg, about 200 about 400 µg, about 1 mg, and about 2 mgs (0.1, 0.3, 0.5, 1.0, 2.0, 4.0, 10.0 and 20.0% w/w) per 20 mg dry powder formulation for administration into one nostril. The formulation may be given in one or both nostrils during each administration. There may be a booster administration 1 to 12 weeks after the first administration to improve the immune response. The content of each VLP/antigen in the vaccine and antigenic formulations may be in the range of 1 µg to 100 mg, preferably in the range 1-1000 µg, more preferably 5-500 µg, most typically in the range 10-200 µg. Total VLP/antigen administered at each dose can be either about 10 µg, about 30 µg, about 200 µg, about 250 µg, about 400 µg, about 500 µg, or about 1000 µg. The total vaccine dose can be administered into one nostril or can be split in half for administration to both nostrils. Dry powder characteristics are such that less than 10% of the particles are less than 10 μm in diameter. Mean particle sizes range from 10 to 500 μm in diameter.

In another embodiment of the invention, the dry powder formulation may be in combination with one or more devices for administering one or more doses of the formulation. Such a device may be a single-use nasal administrative device. In another embodiment, one or more doses are unit doses.

In some embodiments, the antigenic and vaccine formulations are liquid formulations for subsequent administration to a subject. A liquid formulation intended for intranasal administration would comprise chimeric VLP/antigen(s), adjuvant, and a delivery agent such as chitosan. Liquid formulations for parenteral (e.g., subcutaneous, intradermal, or intramuscular (i.m.)) administration would comprise chimeric VLP/antigen(s), adjuvant, and a buffer, without a delivery agent (e.g., chitosan).

Preferably the antigenic and vaccine formulations hereinbefore described are lyophilized and stored anhydrous until they are ready to be used, at which point they are reconstituted with diluent. Alternatively, different components of the composition may be stored separately in a kit (any or all components being lyophilized). The components may remain in lyophilized form for dry formulation or be reconstituted for liquid formulations, and either mixed prior to use or administered separately to the patient. For dry powder administration, the vaccine or antigenic formulation may be preloaded into an intranasal delivery device and stored until use. Preferably, such intranasal delivery device would protect and ensure the stability of its contents.

The present invention provides a method of inducing an immune response to a foreign agent in a subject. In one embodiment, the method comprises administering a vaccine formulation as described herein to the subject, wherein the vaccine formulation comprises a chimeric protein in which the heterologous antigen or fragment thereof present in the chimeric protein is derived from a protein from the foreign agent. The subject may be at risk for acquiring an infection from the foreign agent, may be suffering from an infection from the foreign agent, or may have a recurrent infection caused by the foreign agent. Accordingly, the present invention includes methods of preventing and treating infections associated with foreign agents by administering a vaccine or antigenic formulation of the invention comprising the chimeric proteins described herein that contain heterologous antigens from the foreign agents. In some embodiments, the vaccine or antigenic formulation of the invention comprising a chimeric VLP of the invention does not contain an adjuvant. In other embodiments, the vaccine or antigenic formulation may comprise an adjuvant described herein.

The invention will now be illustrated in greater detail by reference to the specific embodiments described in the following examples. The examples are intended to be purely illustrative of the invention and are not intended to limit its scope in any way.

EXAMPLES

Example 1

Identification of Antigen Insertion Sites in Calicivirus VLPs

The bioreactor production and downstream processing of Norovirus virus-like particles (VLPs) is well-characterized and has been used for initial proof-of-concept studies demonstrating generation of chimeric Calicivirus VLPs. For the GI.1 Norwalk VP1 subunit, identification of surface-exposed loop regions suitable for insertion of foreign epitopes (see FIG. 1A) was carried out by evaluation of the high-resolution x-ray crystal structure (PDB code 1IHM). Similar evaluation of a composite GII.4 Norovirus capsid protein (GII.4 consensus) was conducted (see FIG. 1B) following generation of an atomic structure model using the program Geno3D2. This software uses the atomic structure of homologous proteins as a template (GI.1 Norwalk in the case of GII.2 consensus), and provides a strategy that will similarly be used to generate a structure model for any Calicivirus capsid protein of sufficient sequence similarity and lacking atomic structure data.

Identification of P2 domain surface-exposed loop regions in the Norovirus GI.1 Norwalk and GII.4 consensus VP1 subunits was carried out by analysis of residue accessibility using the Swiss PDB viewer. P2 domain boundaries for Norovirus capsid proteins have been identified previously (see, e.g., Prasad et al. (2000) Journal of Infectious Diseases, Vol. 181: S317-S321). Manual inspection of the atomic structures using the same software confirmed appropriate assignment of P2 domain surface loops. FIG. 1 shows the amino acid sequences of GI.1 Norwalk (1A; SEQ ID NO: 1) and GII.4 consensus (1B; SEQ ID NO: 2) VP1 subunits with P2 domain residues shaded in grey and solvent-accessible loop regions within this domain underlined and denoted by bold font. FIG. 2 shows the GII.4 Consensus structure model (90° rotations) with solvent-accessible P2 domain loops highlighted.

To extend the approaches outlined above to other Calicivirus, structure modeling and identification of solvent-accessible P2 domain loops was additionally carried out for the Sapovirus Hu/Yokohama16-4/2007/JP VP1 subunit. This particular Sapovirus was chosen as it represents a causative agent in human gastroenteritis. For the Calicivirus family, atomic structures are currently available for the Norwalk (Norovirus) and San Miguel sea lion (SMSV; Vesivirus) VP1 capsid proteins. As shown in FIG. 3, evaluation of the Sapovirus capsid protein using the program Geno3D2 generated atomic structure models derived from both Norwalk (FIG. 3A) and the SMSV (FIG. 3B) VP1 subunits as structural templates.

Identification of P2 domain surface-exposed loop regions for each of the Sapovirus VP1 structure models was carried out by analysis of residue accessibility using the Swiss PDB viewer. P2 domain boundaries for the Sapovirus capsid protein were defined by sequence alignment with the templates used for structure modeling. FIG. 4 shows the amino acid sequence of the Hu/Yokohama16-4/2007/JP VP1 subunit (SEQ ID NO: 3) with P2 domain residues shaded in grey and solvent-accessible loop regions within this domain underlined and denoted by bold font.

The above analysis demonstrates substantial differences in both the structure models and identified surface P2 domain loops depending on the atomic structure used as the template for model generation. Despite the fact that both capsid proteins belong to the Calicivirus family, significant structural differences between the Norwalk and SMSV VP1 subunits are not unanticipated in light of the relatively low overall sequence identity and large gaps in the sequence alignment (FIG. 5; P2 domain residues shaded in grey). The generation of atomic structure models for additional Calicivirus subunits is carried out using an available template structure showing the greatest sequence homology with the target. Alternatively, structure models for additional Calicivirus subunits use numerous available Calicivirus VP1 structures in cases where sequence homologies are roughly equivalent. The use of multiple structure templates in cases of similar sequence homology with the target is designed to increase the probability of successful identification of suitable epitope insertion sites.

Example 2

Insertion of Foreign Epitopes in Calicivirus VP1 Open Reading Frames

Two distinct strategies were employed for a comprehensive screening of foreign epitope insertion into preferred sites of the GI.1 Norwalk VP1 subunit: 1) simple insertions at various residue positions in solvent-accessible loops of the P2 domain; and 2) replacement of solvent-accessible loop residues of the P2 domain.

Mutagenesis involving inserts of 9 amino acids was conducted using appropriate synthetic oligonucleotides as mutagenic primers, while constructs with larger inserts were generated by gene synthesis. An alternative strategy for generation of chimeric VLPs with larger inserts involves engineering unique restriction sites into desired regions of the VP1 reading frame in order to ligate either synthetic DNA or PCR products encoding the appropriate epitope sequences. Similar strategies are carried out for epitope insertion in additional Calicivirus capsid proteins.

Figure 6:
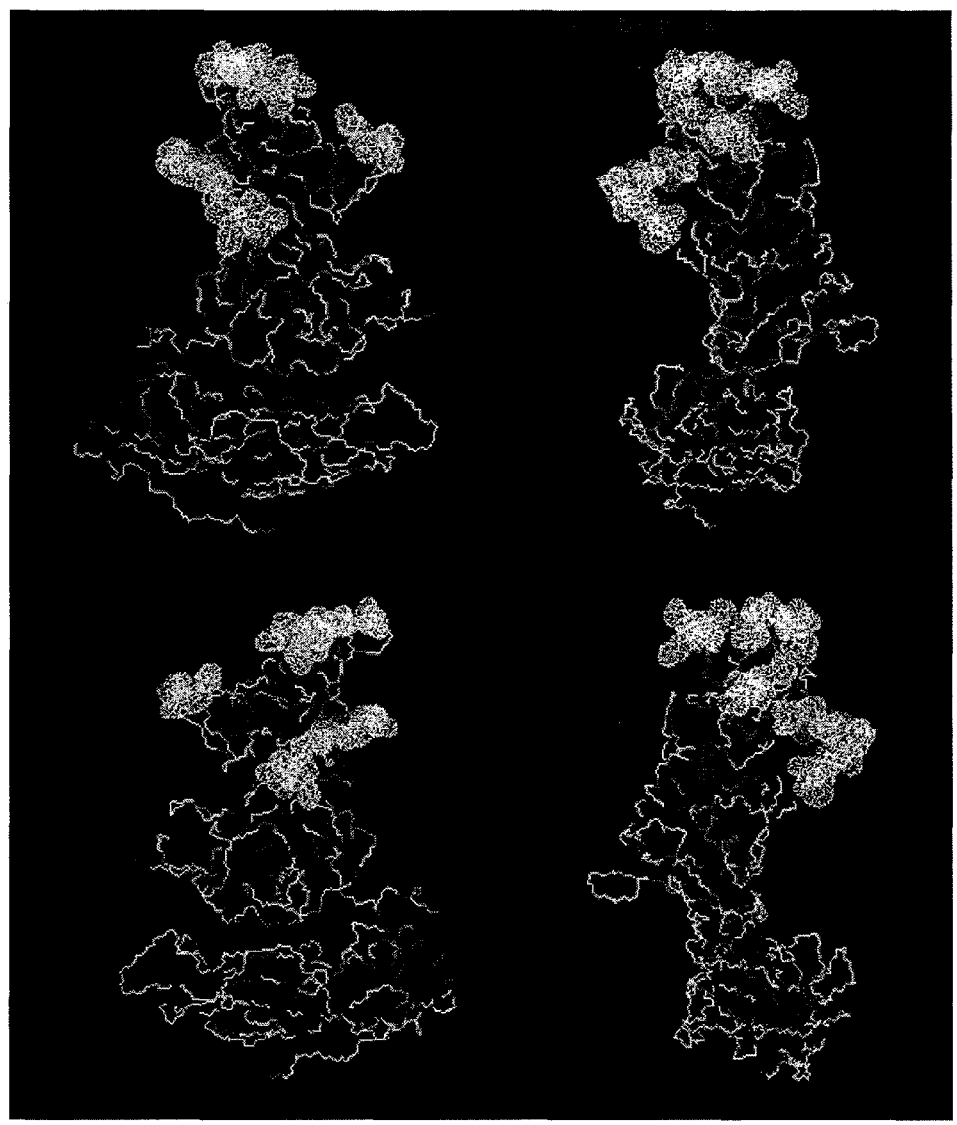
FIG. 6. Residue replacement and insertion sites (highlighted) of foreign epitope in the Norovirus GI.1 Norwalk VP1 subunit.

For first generation constructs, PCR mutagenesis was used to insert a model epitope in the Norwalk VP1 subunit using the QuickChange Lightning mutagenesis kit (Stratagene; La Jolla, Calif.). Constructs were generated using a shuttle vector containing Norwalk VP1 as the DNA template, with the resulting chimeric sequences confirmed by PCR and DNA sequence analysis. The chimeric VP1 reading frames were then subcloned into the transfer vector pVL1393 to enable generation of recombinant baculovirus. If PCR amplification was used prior to generating the insert for subcloning, the final reading frame was confirmed by DNA sequence analysis. This approach allows for rapid and efficient generation of numerous epitope/insert site combinations. Chimeric VP1 reading frames with larger epitope insertions were generated by DNA synthesis, with subsequent subcloning into the transfer vector pVL1393 to enable generation of recombinant baculovirus. FIG. 6 shows the Norwalk VP1 x-ray structure (90° rotations) with residues that have been replaced with a foreign antigen highlighted. The first generation constructs shown in FIG. 6 represent 5 solvent-exposed loop residues in the P2 domain that have been replaced with a 9 amino acid model epitope (See Example 3). First generation constructs have also been generated containing direct insertion of a model epitope between select residues in the loops highlighted in FIG. 6 (i.e., without deletion of any VP1 residues). See Example 1 and FIG. 1A for location of solvent-exposed residues in Norwalk VP1 amino acid sequence.

Example 3

Production of Chimeric Calicivirus VLPs

Figure 7:
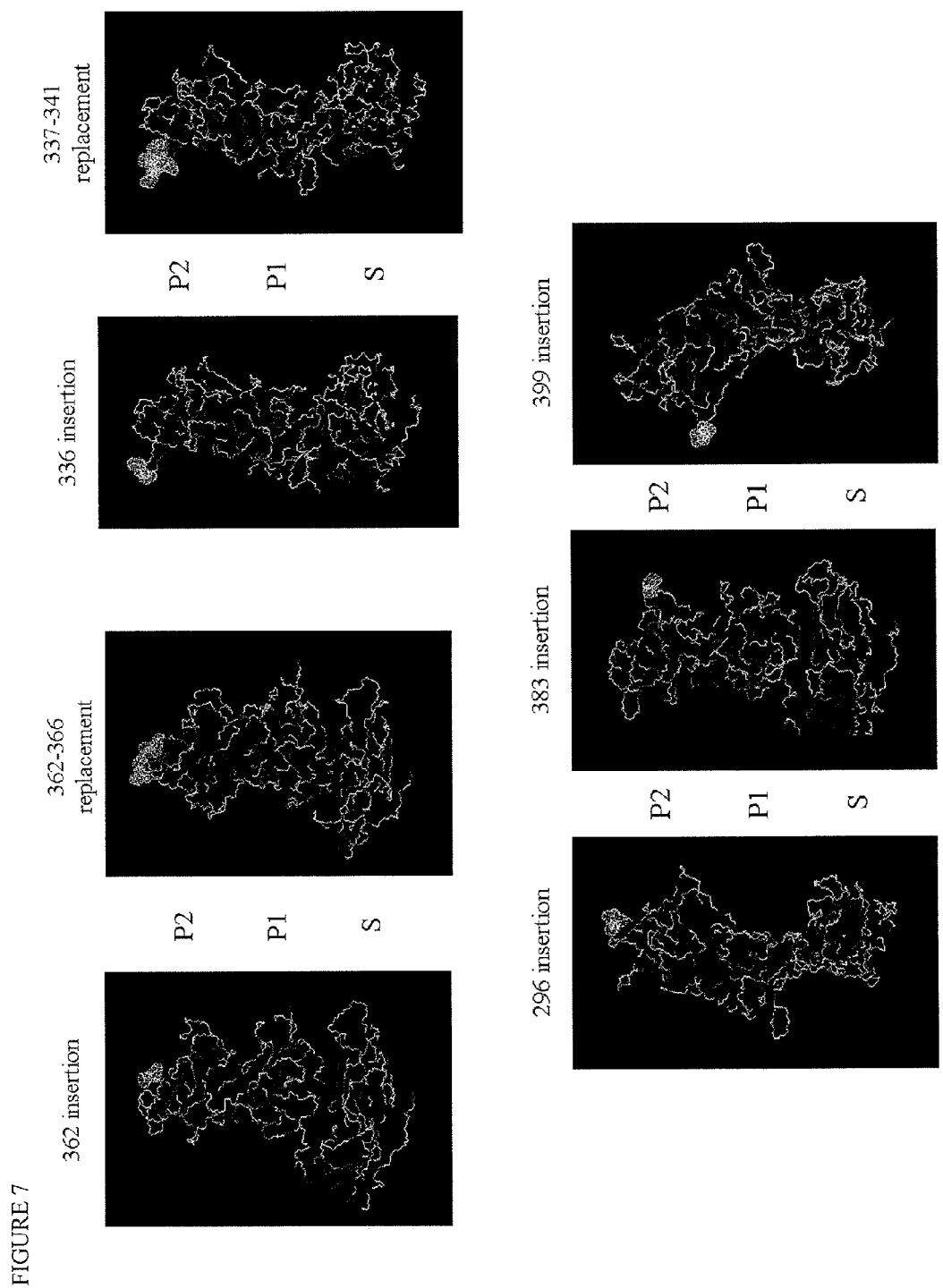
FIG. 7. Epitope insertion and partial replacement sites for chimeric Norwalk VLPs. A nine amino acid epitope derived from influenza hemagglutinin antigen (SEQ ID NO: 5) either was inserted directly after the indicated amino acid residues or replaced the indicated residues in the Norwalk VP1 protein sequence.

Generation of recombinant baculovirus encoding chimeric Norwalk VP1 subunits was conducted by co-transfection of transfer vector (pVL1393-Norwalk VP1) and linear baculovirus DNA into adherent Sf9 insect cells, followed by further virus expansion to generate high-titer stocks. As an initial proof-of-concept screen for production of chimeric VLPs, a model epitope derived from the influenza hemagglutinin antigen (HA epitope sequence-YPYDVPDYA (SEQ ID NO: 5)) was directly inserted after Norwalk VP1 residue 296, 336, 362, 383 or 399. In addition, expression trials were conducted for constructs where this model antigen replaced Norwalk VP1 residues 337-341 or residues 362-366. FIG. 7 shows Norwalk VP1 residues that either contain a direct insertion or have been replaced by the model hemagglutinin epitope.

Figure 8:
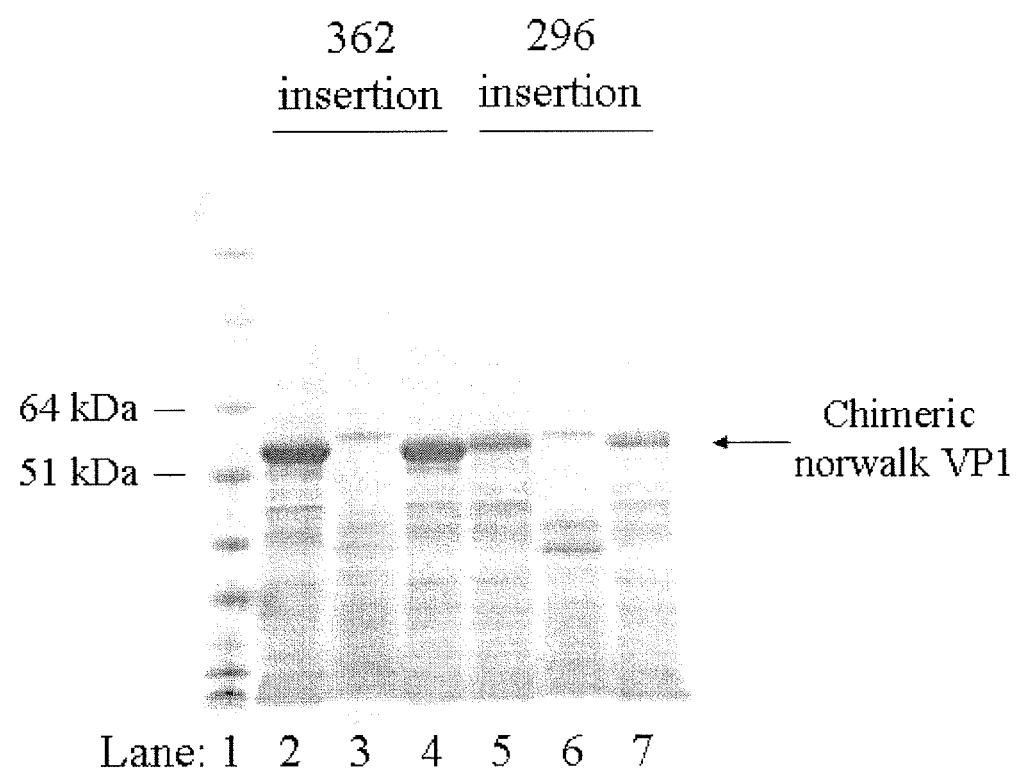
FIG. 8. SDS-PAGE analysis of chimeric Norwalk VLP production. A nine amino acid epitope derived from influenza hemagglutinin antigen was inserted directly after amino acid residue 362 or 296 in the Norwalk VP1 protein sequence. Virus-like particles were generated from the modified VP1 sequences and analyzed by SDS-PAGE. Lane 1, molecular weight standards; lane 2, 362 insertion post-centrifuge supernatant; lane 3, 362 centrifuge pellet fraction; lane 4, 362 insertion filtrate; lane 5, 296 insertion post-centrifuge supernatant; lane 6, 296 centrifuge pellet fraction; and lane 7, 296 insertion filtrate. Protein bands at about 57 kDa represent chimeric Norwalk VP1 protein.

For production of chimeric VLPs, Sf9 insect cells were grown to $2\times10^6$ cells/ml in 50 mL spinner-flask cultures and then infected with P1 stocks of recombinant baculovirus at an estimated multiplicity of infection (MOI)=1.0. Following infection, cultures were harvested by low-speed centrifugation and subsequent clarification with a 0.2 µm filter at T=96 to 120 h post-infection where VLPs were released into the culture supernatant as a result of natural cell lysis. The SDS-PAGE analysis shown in FIG. 8 depicts the results from expression studies for chimeric Norwalk VLPs containing the model HA antigen inserted after VP1 residue 296 or 362 (Lane 1, molecular weight standards; lane 2, 362 insertion post-centrifuge supernatant; lane 3, 362 centrifuge pellet fraction; lane 4, 362 insertion filtrate; lane 5, 296 insertion post-centrifuge supernatant; lane 6, 296 centrifuge pellet fraction; and lane 7, 296 insertion filtrate). The prominent Norwalk VP1 band migrating at the anticipated molecular weight (~57 kDa) in the post-centrifuge supernatant (lane 2) and filtrate (lane 4) fractions for the 362 insertion chimera displays an expression pattern similar to native Norwalk VP1, and demonstrates the ability of this solvent-accessible P2 loop to efficiently tolerate foreign antigen insertion. FIG. 8 also shows much lower VP1 expression levels in the above fractions for constructs containing the model HA epitope inserted directly after norwalk VP1 residue 296 (lanes 5 and 7). In these studies, diminished expression of the 296 insertion construct results from proteolysis of the VP1 subunit prior to cell lysis, which likely results from a lack of VLP assembly for a portion of the VP1 subunit, and demonstrates that mere identification of a surface exposed loop is not sufficient to ensure efficient production of chimeric VLPs.

Figure 9:
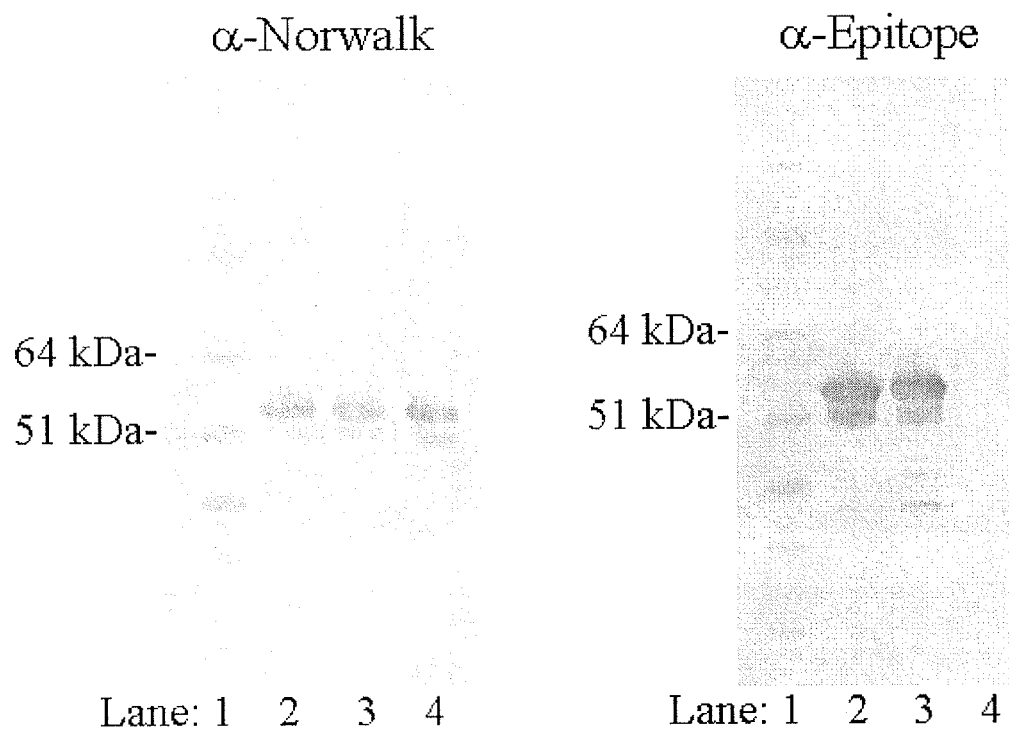
FIG. 9. Western blot analysis of chimeric Norwalk VLP production. Western blots of chimeric VLPs containing a hemagglutinin (HA) epitope were probed with an anti-Norwalk antibody (left panel) or an anti-HA antibody (right panel). Lane 1, molecular weight standards; lane 2, chimeric VLPs with HA epitope insertion at VP1 residue 336; lane 3, chimeric VLPs with HA epitope replacement of VP1 residues 337-341; and lane 4, wild-type Norwalk VP1. Protein bands at about 57 kDa represent chimeric Norwalk VP1 protein.

The ability to generate chimeric VLPs using the above strategy is confirmed in FIG. 9 for the Norwalk VP1 subunit containing the model HA epitope inserted after VP1 residue 336 or replacing residues 337-341. Western blot analysis was used to demonstrate an SDS-PAGE band migrating at the anticipated molecular weight (~57 kDa) showed specific and appropriate reactivity with anti-Norwalk and anti-HA epitope monoclonal antibodies (Lane 1, molecular weight standards; lane 2, chimeric VLPs with epitope insertion at VP1 residue 336; lane 3, chimeric VLPs with epitope replacement of VP1 residues 337-341; and lane 4, wild-type Norwalk VP1).

Figure 10:
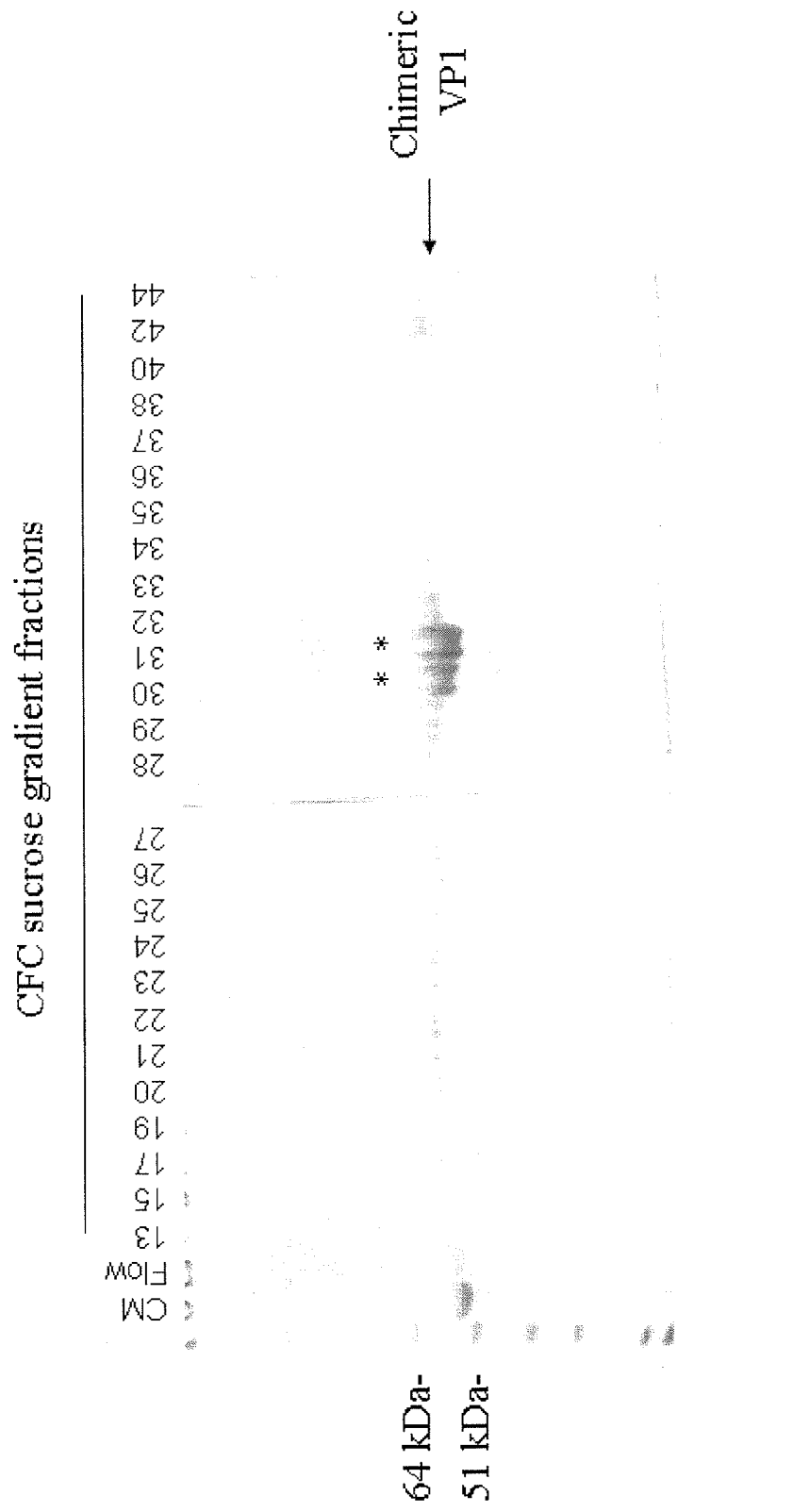
FIG. 10. Purification of chimeric Norwalk VLPs by continuous flow centrifugation (CFC). The asterisks represent intact chimeric Norwalk VLPs.

For small-scale expression and purification of chimeric Norwalk VLPs, Sf9 insect cells were grown to $2\times10^6$ cells/ml in Sf-900 II media (1 L shake flask cultures) and then infected with recombinant baculovirus at MOI=0.5. Following VLP expression (96 to 120 h post-infection), cultures were harvested by low-speed centrifugation and subsequent clarification using a 0.2 µm filter. Since assembled VLPs have a characteristically high molecular weight (~10 MDa), material can be readily purified by methods that do not depend on surface chemistry, such as sucrose-gradient centrifugation and size-exclusion chromatography. FIG. 10 shows purification of chimeric Norwalk VLPs (336 insertion) by continuous flow centrifugation (CFC), where purification starting material was isolated on a 0-60% linear sucrose gradient by centrifugation at 100,000×g for ~16 h using a TCF-32 rotor. This analysis demonstrates high-level production of chimeric VLPs in the starting conditioned media (CM) and a prominent peak of the chimeric VP1 subunit that bands at a sucrose density that is anticipated for virus-like particles.

Example 4

Characterization of Chimeric Calicivirus VLPs

Figure 11:
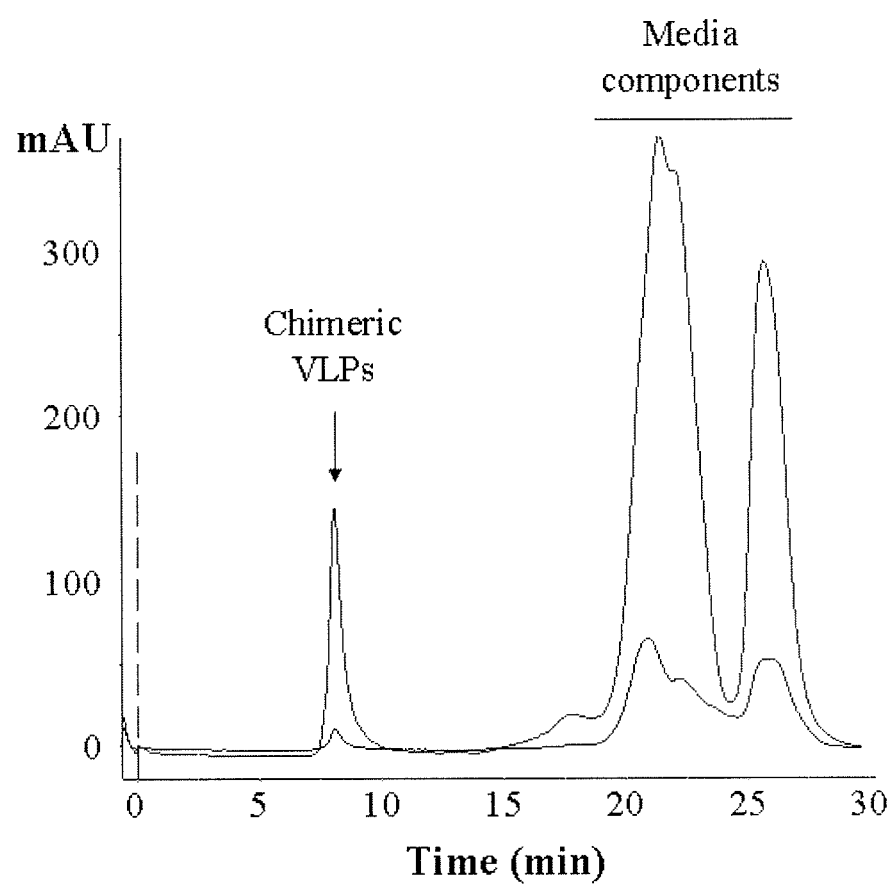
FIG. 11. Analysis of chimeric Norwalk VLPs by size-exclusion chromatography. Red trace-absorption at 220 nm; blue trace-absorption at 280 nm.

To ensure appropriate protein expression and VLP formation for chimeric Calicivirus VP1 subunits, a number of analytical methods are used for characterization throughout the production process including SDS-PAGE, Western blot analysis, high resolution mass spectrometry, size-exclusion chromatography and electron microscopy. The use of SDS-PAGE and Western blot analysis is highlighted in Example 3, where these methods demonstrated appropriate subunit molecular weight and the presence of foreign antigen for chimeric Norwalk VLPs. The high molecular weight of Norovirus VLPs (>10 MDa) allows for direct analysis by size-exclusion chromatography, even in crude purification starting material. The utility of this method for assessing VLP formation is demonstrated in FIG. 11, where the conditioned media for the Norwalk VP1-HA chimera (336 insertion) was analyzed by size-exclusion chromatography. In this study, the presence of a peak with the anticipated retention time (~8 min) demonstrated appropriate formation of chimeric VLPs (red trace-absorption at 220 nm (shown on Y-axis) and blue trace-absorption at 280 nm).

Figure 12:
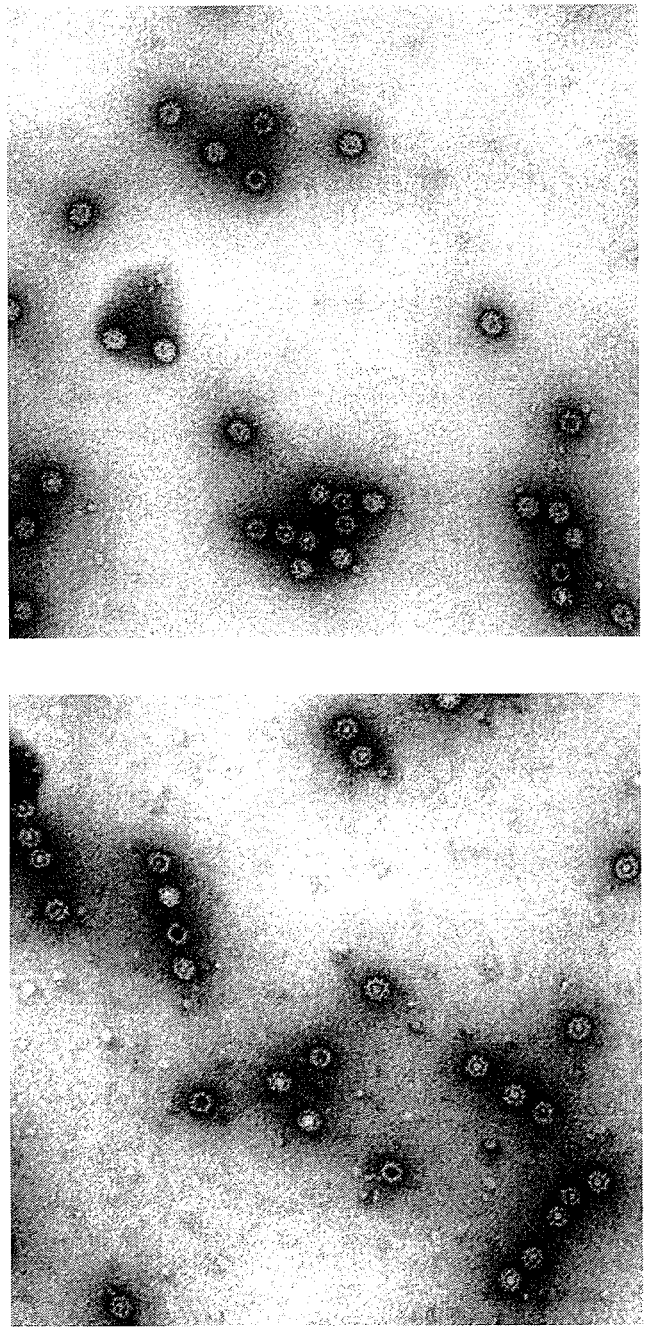
FIG. 12. Analysis of chimeric Norwalk VLPs by electron microscopy.

Appropriate formation of VLPs in pooled continuous flow centrifugation fractions (see Example 3) was additionally confirmed by electron microscopy, which demonstrated anticipated particles of ~32 nm for chimeric Norwalk VLPs containing the model HA epitope inserted after VP1 residue 336 or replacing VP1 residues 337-341 (FIG. 12).

Example 5

Scale-up Bioreactor Production and Downstream Processing of Chimeric Calicivirus VLPs Initial scale-up bioreactor production of chimeric VLPs is carried out using a Wave bioreactor platform and single-use, disposable Wavebags as the bioreactor vessel. These studies focus on the optimization of basic parameters including cell density prior to infection, multiplicity of infection, and time of infection prior to harvest. Initial optimization also includes screening of multiple insect cell line/media combinations and media supplementation. These studies serve to both develop scalable production strategies and supply material for downstream processing. Bioreactor productivities ranging from >50 mg/L have been routinely observed for Norovirus VLPs using the Wave bioreactor system and a variety of insect cell/serum-free media combinations.

Downstream processing of chimeric VLPs from harvested bioreactor cultures is carried out by well-established and scalable methods including conventional chromatography, membrane chromatography, and tangential flow filtration. For chromatographic screening, initial pilot studies are conducted on a small-scale in order to optimize binding/elution conditions, evaluate effects of flow rate, estimate step recoveries and characterize purification factors with regard to host cell protein/nucleic acid.

Example 6

Additional Approaches for the Presentation of Foreign Epitopes

As outlined in Example 1, preferred sites for insertion of foreign epitopes have been based on the identification of solvent-accessible P2 domain surface loops by evaluation of Calicivirus VP1 atomic structure models. As a complimentary approach to identification of optimal positions for epitope insertion, the above structure analysis is combined with amino acid sequence and biochemical data to aid in identification of permissive sites. Amino acid sequence data is used in multiple alignments to identify hypervariable P2 domain residues that fall within the surface loop regions identified by structure analysis. Positions identified by both measures are considered optimal for direct insertion of foreign epitope sequences. Similarly, positions with multiple hypervariable P2 residues that fall within a single surface exposed loop identified by structure analysis is considered optimal for partial replacement of VP1 residues and will provide guidance in establishing VP1 deletion boundaries. The use of biochemical data, such as the identification of P2 domain residues of Calicivirus escape mutants and/or antibody epitopes, additionally serves to highlight suitable positions for the insertion of foreign epitopes.

As outlined in Examples 2-4, foreign epitope insertions of 9 amino acids were used for the generation of first-generation chimeric Norwalk VLPs. To optimize VLP production and/or foreign epitope immunogenicity, inserted epitope sequences of various lengths are evaluated, including sequences of 5-10 residues, 11-20 residues, 21-30 residues, 31-40 residues or 41-50 residues. Since the deletion of Calicivirus residues may represent a critical factor for insertion of foreign epitopes, VP1 deletions of various lengths are evaluated including 5-10 residues, 11-20 residues, 21-30 residues, 31-40 residues or 41-50 residues.

Recombinant expression of chimeric VLPs can involve the insertion of multiple foreign antigens simultaneously into two or more solvent accessible loops of the Calicivirus P2 domain. Since several of the identified loops reside in relatively close spatial proximity, the insertion of multiple loops can be engineered such that there is direct contact of inserted sequences to form discontinuous epitopes.

For expression of chimeric Calicivirus VLPs, target antigens can be derived from mimotope sequences or composite linear sequences representing discontinuous epitopes. Mimotope sequences are linear peptides that bind neutralizing antibodies with high affinity, but do not represent an actual amino acid sequence found in the target antigen. Sequences of this nature are either derived from the literature or are determined by epitope mapping neutralizing antibodies by methods such as phage display analysis or combinatorial peptide libraries. Composite linear sequences that represent discontinuous epitopes can be similarly derived from the literature, from combinatorial methods or from structure analysis of antibody:antigen complexes.

To enhance the efficiency of chimeric VLP production, a platform can be designed to structurally constrain the conformational space of foreign epitope sequences to better conform to Calicivirus VP1 surface loop boundaries. This objective is carried out by engineering covalent or non-covalent protein-protein interaction motifs into either the surface-exposed loops of the VP1 subunit or the foreign antigen sequence.

A variation on the approaches outlined above involves the generation of chimeric VLPs where only a subfraction of the VP1 subunits display a foreign epitope on solvent-accessible loops of the P2 domain. This strategy may prove critical for maintaining desired VLP assembly, particularly in cases where relatively large foreign epitopes are inserted in the VP1 subunit. To generate VLPs of this nature, individual Calicivirus VP1 subunits (both native and modified) are initially produced in a highly purified state that is suitable for VLP assembly (i.e., fully denatured monomers, monomers containing native-like secondary/tertiary structure, or lower-order VP1 assembly states). Chimeric VLPs are then generated by mixing the native and modified subunits at the desired ratio and establishing conditions that promote efficient VLP assembly. Alternatively, VLPs of this nature are directly produced in culture by generating constructs where expression of the native and modified subunits is regulated by two different promoters. Using this approach, the native VP1 subunit is placed under a relatively strong promoter to drive expression levels that exceed those of the modified subunit. Assembly of chimeric VLPs takes place in the cell with modified VP1 subunit displayed on a subfraction of the VLP surface.

A further variation that can create a more universal display platform involves the generation of Norovirus VLPs that contain a target sequence that promotes specific, high-affinity binding of desired foreign antigens (e.g., contain a complimentary binding motif) to solvent-accessible P2 domain surfaces. To generate chimeric VLPs of this nature, the Norovirus subunit and target antigen are expressed and purified separately, and then mixed under conditions that allow binding. Using this approach, the target antigen is bound to the VP1 subunit on fully assembled VLPs or to the VP1 subunit prior to VLP assembly. To evaluate conditions that provide optimal VLP stability and antigen presentation, chimeric VLPs are generated by expressing the target sequence on each copy or only a subset of the VP1 subunits.

Example 7

Immunization of Mice with Chimeric Norwalk VLPs

Female C57/BL6 mice, approximately 10-12 weeks of age, are immunized intraperitoneally with 30 µg native Norwalk VLPs or one of the chimeric Norwalk VLPs described in Example 3 (e.g., HA eptiope inserted after 296, 336, 362, 383 or 399 residue of Norwalk VP1 or replacement of Norwalk VP1 residues 337-341 or residues 362-366 with the HA epitope). The mice are bled on day 21 following immunization and the sera are assayed in an antigen-specific ELISA to determine antibody titers for the native and chimeric Norwalk VLPs. The results are expected to show that chimeric VLPs produce significant titers for both anti-Norwalk and anti-HA antibodies.

Example 8

Figure 13:
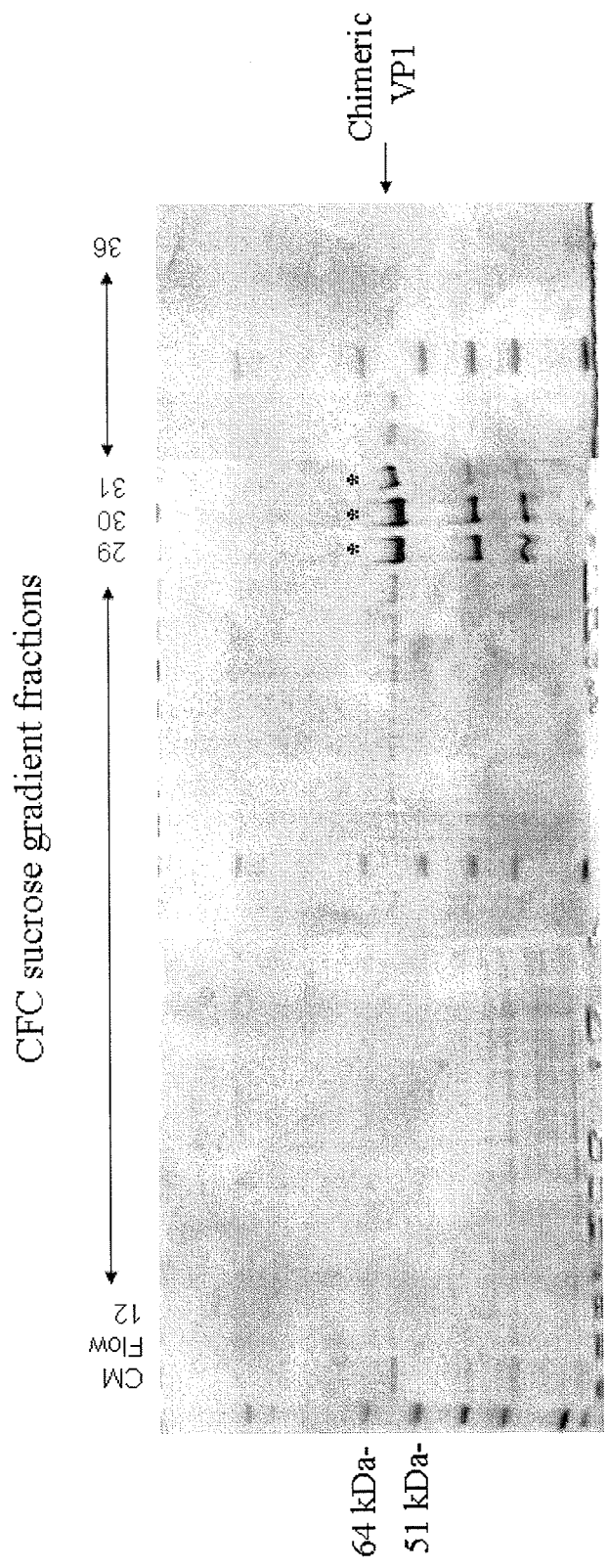
FIG. 13. Purification of chimeric Norwalk VLPs (containing a 29 residue RSV-F protein epitope) by continuous flow centrifugation (CFC). The asterisks represent intact chimeric Norwalk VLPs.
Figure 15:
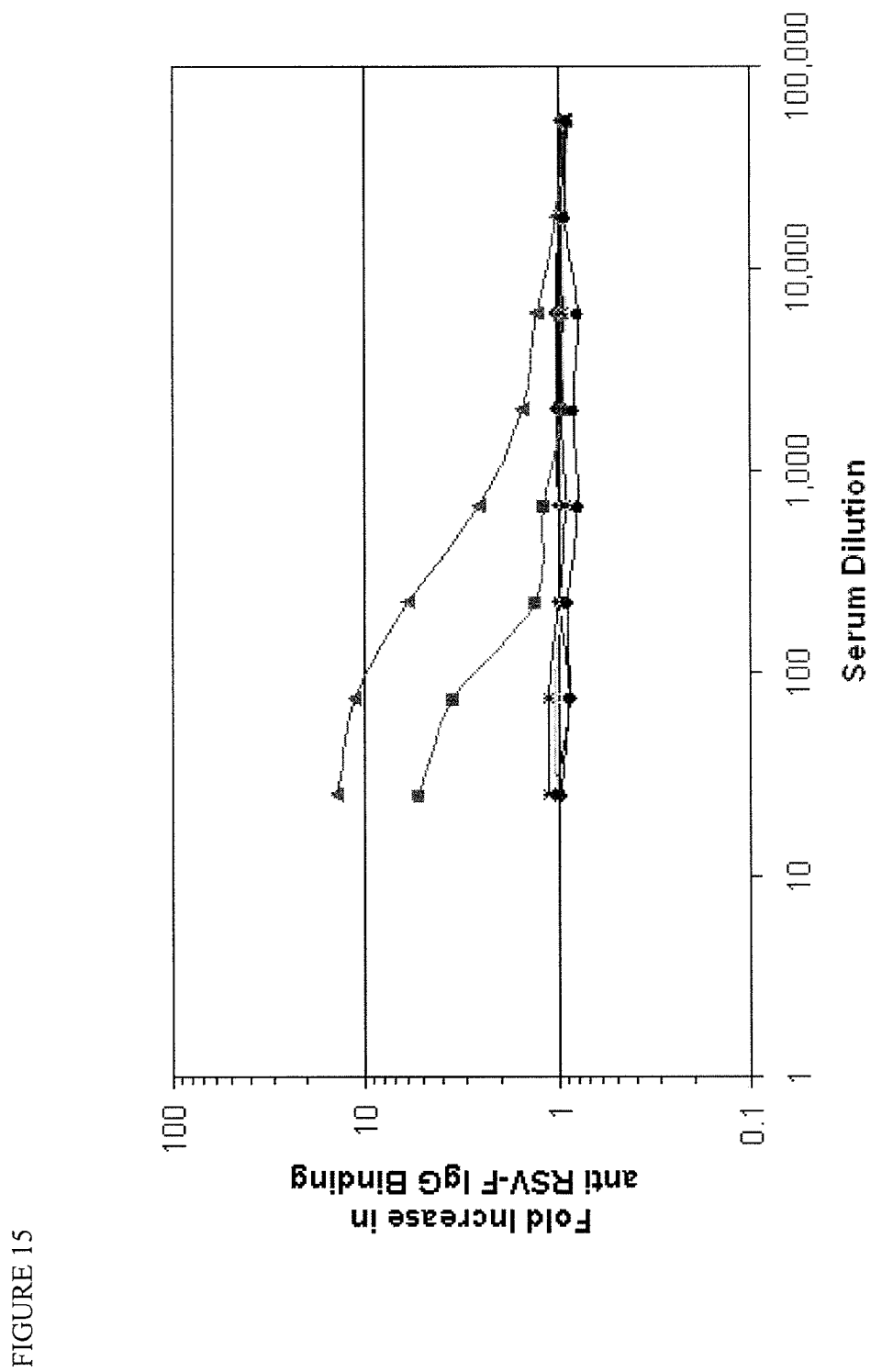
FIG. 15. Fold increase in OD as a function of serum dilution where 2 of 6 animals showed a greater than 4 fold increase in antiRSV-F IgG antibodies.

Production, Characterization and Immunogenicity of Chimeric Calicivirus VLPs Containing a 29 Residue, Medically-Relevant Foreign Antigen To generate chimeric norovirus VLPs containing a larger, medically-relevant foreign antigen, a 29 amino acid sequence derived from the Respiratory Syncytial Virus (RSV) F protein (RSV F epitope sequence-YMLTNSELLSLINDMPIT-NDQKKLMSNNV (SEQ ID NO: 7), which is recognized by the neutralizing antibody Synagis) was directly inserted after Norwalk VP1 residue 308, 338, or 363. In addition, constructs were generated containing the RSV F epitope replacing Norwalk VP1 residues 307-311, 337-341 or residues 362-366. Following the generation of recombinant baculovirus and VLP production in Sf9 insect cells, the chimeric VLPs were purified, characterized and examined for immunogenicity. FIG. 13 shows purification of chimeric Norwalk VLPs (308 insertion) by continuous flow centrifugation (CFC), where purification starting material was isolated on a 0-60% linear sucrose gradient by centrifugation at 100,000×g for ~16 h using a TCF-32 rotor. This analysis demonstrates production of chimeric VLPs in the starting conditioned media (CM) and a prominent peak of the chimeric VP1 subunit that bands at a sucrose density expected for virus-like particles. The formation of VLPs in material purified by continuous flow centrifugation was confirmed by transmission electron microscopy (FIG. 14). To evaluate immunogenicity, the CFC-purified chimeric VLPs were formulated at 200 µg/mL in 20 mM Histidine (pH-6.5), 150 mM NaCl. Six Balb/c mice were immunized with 20 µg chimeric VLPs (~1 µg RSV epitope) on study day 0 and boosted with an additional 20 µg chimeric VLP on study day 21. Blood was collected on study day 35 and analyzed for total IgG titers using both RSV-F and Norwalk protein specific ELISAs. In this study, 2 of the 6 animals dosed with the chimeric VLP also showed a greater than 4 fold increases in anti RSV-F IgG (FIG. 15).

Example 9

Figure 16:
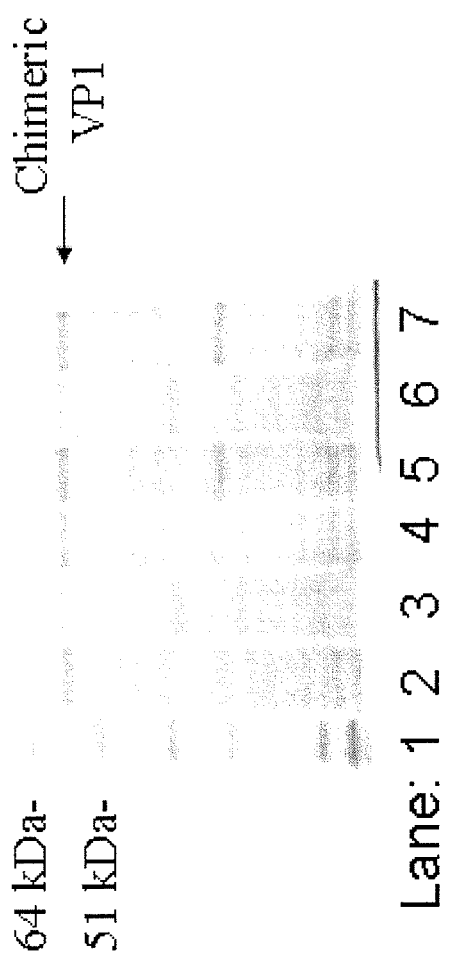
FIG. 16. SDS-PAGE analysis of chimeric Norwalk VLP production containing two modified surface loops. A nine amino acid epitope derived from the RSV-F antigen was inserted simultaneously at residues 338 and 363, or simultaneously replacing residues 337-341 and inserted at residue 363. Virus-like particles were generated from the modified VP1 sequences and analyzed by SDS-PAGE. Lane 1, molecular weight standards; lane 2, 338 and 363 insertion post-centrifuge supernatant; lane 3, 338 and 363 insertion centrifuge pellet fraction; lane 4, 338 and 363 insertion filtrate; lane 5, 337-341 replacement and 363 insertion post-centrifuge supernatant; lane 6, 337-341 replacement and 363 insertion centrifuge pellet fraction; and lane 7, 337-341 replacement and 363 insertion filtrate. Protein bands at about 57 kDa represent chimeric Norwalk VP1 protein.

Production of Chimeric Calicivirus VLPs Containing Multiple Modified Surface Loops To generate chimeric norovirus VLPs containing multiple modified loops, a 9 amino acid sequence of the RSV F protein (RSV F epitope sequence-LINDMPITN (SEQ ID NO: 6)) was added to two Norwalk VP1 surface loops within the same construct. In these studies, constructs were generated containing the RSV F epitope inserted simultaneously at residues 338 and 363, or simultaneously replacing residues 337-341 and inserted at residue 363. The SDS-PAGE analysis shown in FIG. 16 depicts the results from expression studies for chimeric Norwalk VLPs containing the 9 residue RSV-F antigen (Lane 1, molecular weight standards; lane 2, 338 and 363 insertion post-centrifuge supernatant; lane 3, 338 and 363 insertion centrifuge pellet fraction; lane 4, 338 and 363 insertion filtrate; lane 5, 337-341 replacement and 363 insertion post-centrifuge supernatant; lane 6, 337-341 replacement and 363 insertion centrifuge pellet fraction; and lane 7, 337-341 replacement and 363 insertion filtrate). The prominent Norwalk VP1 band migrating at the expected molecular weight (~57 kDa) in the post-centrifuge supernatant (lanes 2 and 5) and filtrate (lanes 4 and 7) fractions for each of the chimera displays an expression pattern similar to native Norwalk VP1, and demonstrates the ability of this solvent-accessible P2 loop to efficiently tolerate foreign antigen insertion. For these chimeras particle formation was indicated by SEC data and these studies support concepts outlined in Example 6.

Example 10

Immunogenicity of Chimeric Calicivirus VLPs Containing a Hemagglutinin Epitope

Figure 17:
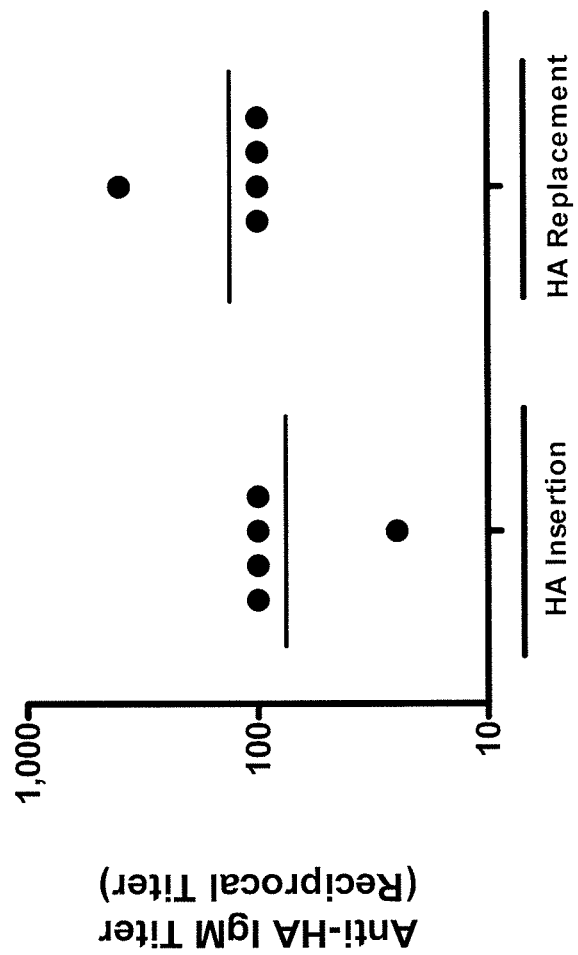
FIG. 17. The HA protein sequence was either inserted in between amino acids 338 and 339 of the Norwalk VP1 protein or it replaced amino acids 337-341 of VP1. The HA-NVLP was administered intraperitoneally on days 0 and 7 without adjuvant. Serum was collected on day 14 and analyzed for the presence of antigen-specific IgM by ELISA. Individual results are shown with the horizontal bars representing the group geometric means.
Figure 18:
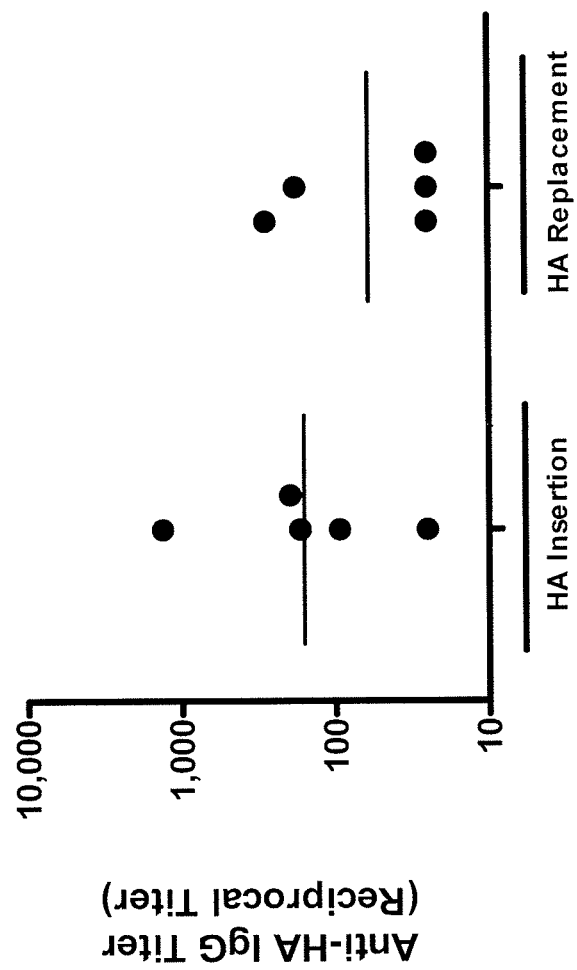
FIG. 18. The mice from FIG. 17 received an additional immunization on day 37 of the HA-NVLP formulated with AlOH/MPL. Serum was collected on day 64 and analyzed for the presence of HA-specific IgG by ELISA. Individual results are shown with the horizontal bars representing the group geometric means.

A model epitope derived from the influenza hemagglutinin antigen (HA epitope sequence-YPYDVPDYA (SEQ ID NO: 5)) was directly inserted between Norwalk VP1 residue amino acids 338-339 on the VP1 and designated herein as "HA insertion." An additional construct was made where the HA epitope replaced Norwalk VP1 residue amino acids 337-341 in VP1 and designated herein as "HA replacement." The total protein content was determined for each construct prior to immunization. The "HA-insertion" construct was determined to contain 34 µg/ml of total protein and the "HA-replacement" construct was determined to contain 42 µg/ml of total protein. Fifty microliters were removed from each tube and injected in a mouse intraperitoneally on day 0 and 7. Serum was collected on day 14, but no measureable antigen-specific IgG could be detected by ELISA. However, low levels of HA-specific IgM could be detected in nearly all mice (FIG. 17). Since the HA content of the chimeric VLPs is only 1.7% of the total protein a possible reason for the IgM-only response is low HA concentration (29 ng HA for the "HA-insertion" and 36 ng HA for the "HA replacement"). To determine if the presence of adjuvant would enhance the immune response to HA, chimeric VLPs adsorbed onto AlOH/MPL were given to the previously treated mice on day 37. Serum was collected on day 64 and analyzed for HA-specific IgG (FIG. 18). The addition of the adjuvant resulted in four of five mice immunized with "HA-insertion" and two out of five mice immunized with the "HA-replacement" having a detectable HA-specific IgG response. All of the mice in this study produced Norwalk-specific IgG that were similar to historic values. In conclusion, the HA epitope is presented and visible to the immune system. At the low concentrations of HA antigen used in this study, an adjuvant can be used to increase the immune response. Alternatively, increasing the amount of HA eptiope would be expected to increase the immune response.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

The invention claimed is:

1. A chimeric protein comprising a Norovirus capsid protein having a P2 domain and at least one heterologous antigen or fragment thereof, wherein said at least one heterologous antigen or fragment thereof is inserted into said P2 domain of said capsid protein, and wherein the heterologous antigen or fragment thereof is not from any calicivirus said chimeric protein is capable of forming virus-like particles when expressed in a host cell.

2. The chimeric protein of claim 1, wherein said at least one heterologous antigen or fragment thereof is inserted into at least one solvent-exposed loop of said P2 domain.

3. The chimeric protein of claim 1, wherein said capsid protein is VP1.

4. The chimeric protein of claim 3, wherein said capsid protein has an amino acid sequence of SEQ ID NO: 1.

5. The chimeric protein of claim 4, wherein said at least one heterologous antigen or fragment thereof is inserted directly into SEQ ID NO: 1 after the asparagine residue at position 295, the glycine residue at position 296, the proline residue at position 308, the glycine residue at position 336, the serine residue at position 338, the asparagine residue at position 362, the glycine residue at position 363, the proline residue at position 382, the serine residue at position 383, the isoleucine residue at position 399, or the alanine residue at position 402.

6. The chimeric protein of claim 4, wherein said at least one heterologous antigen or fragment thereof replaces amino acids 294-298, amino acids 307-311, amino acids 337-341, amino acids 362-366, amino acids 381-385, or amino acids 401-405 of SEQ ID NO: 1.

7. The chimeric protein of claim 1, wherein said capsid protein is a composite capsid protein that incorporates amino acid sequences from two or more circulating strains of Norovirus.

8. The chimeric protein of claim 7, wherein said composite capsid protein has an amino acid sequence of SEQ ID NO: 2.

9. The chimeric protein of claim 1, where said Norovirus is a Genogroup I or Genogroup II Norovirus.

10. The chimeric protein of claim 9, wherein said Norovirus is a Genogroup I, genotype I Norovirus or Genogroup II, genotype 4 Norovirus.

11. The chimeric protein of claim 1, wherein said at least one heterologous antigen or fragment thereof comprises an antigenic epitope.

12. The chimeric protein of claim 1, wherein said at least one heterologous antigen or fragment thereof is from a virus, bacteria, eukaryotic pathogen, tumor-associated antigen, or allergen.

13. The chimeric protein of claim 12, wherein said at least one heterologous antigen or fragment thereof is from a virus selected from the group consisting of rotavirus, respiratory syncytial virus, parainfluenza virus, and metaneumovirus.

14. A virus-like particle comprising the chimeric protein of claim 1.

15. A vaccine formulation comprising the virus-like particle of claim 14.

16. The vaccine formulation of claim 15 further comprising an adjuvant.

17. An isolated nucleic acid encoding the chimeric protein of claim 1.

18. A vector comprising the isolated nucleic acid of claim 17.

19. An isolated host cell comprising the vector of claim 18.

20. The isolated host cell of claim 19, wherein the host cell is a bacterial cell, an insect cell, a yeast cell, or a mammalian cell.

21. A method of making a chimeric virus-like particle comprising:

expressing the chimeric protein of claim 1 in a host cell; and growing said host cell in conditions in which virus-like particles are formed.

22. The method of claim 21, wherein said at least one heterologous antigen or fragment thereof is fused to at least one solvent-exposed loop of said P2 domain.

23. The method of claim 21, wherein said at least one heterologous antigen or fragment thereof comprises an antigenic epitope.

24. The method of claim 21, where said Norovirus is a Genogroup I or Genogroup II Norovirus.

25. The method of claim 24, wherein said Norovirus is a Genogroup I, genotype I Norovirus or a Genogroup II, genotype 4 Norovirus.

26. A method of inducing an immune response to a foreign agent comprising administering the vaccine formulation of claim 15 to a subject, wherein the at least one heterologous antigen or fragment thereof is from a protein from the foreign agent.

* * * * *